(12) United States Patent
Matsuura et al.

(10) Patent No.: US 11,542,523 B2
(45) Date of Patent: Jan. 3, 2023

(54) ANIMAL CELL, METHOD FOR PRODUCING ANIMAL CELL, AND METHOD FOR PRODUCING TARGET PROTEIN

(71) Applicant: FUJIFILM Corporation, Tokyo (JP)

(72) Inventors: Tatsuya Matsuura, Ashigarakami-gun (JP); Tsukasa Ishihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 258 days.

(21) Appl. No.: 16/897,860

(22) Filed: Jun. 10, 2020

(65) Prior Publication Data

US 2020/0299723 A1 Sep. 24, 2020

Related U.S. Application Data

(63) Continuation of application No. PCT/JP2018/045479, filed on Dec. 11, 2018.

(30) Foreign Application Priority Data

Dec. 11, 2017 (JP) .................................. 2017-236641

(51) Int. Cl.
| | |
|---|---|
| *C12N 15/85* | (2006.01) |
| *C07K 16/00* | (2006.01) |
| *C12N 5/071* | (2010.01) |
| *C12N 9/02* | (2006.01) |
| *C12N 15/87* | (2006.01) |

(52) U.S. Cl.
CPC .............. *C12N 15/85* (2013.01); *C07K 16/00* (2013.01); *C12N 5/0682* (2013.01); *C12N 9/001* (2013.01); *C12N 15/87* (2013.01); *C12Y 103/08004* (2015.07)

(58) Field of Classification Search
CPC ........ C12N 15/85; C12N 15/87; C12N 9/001; C12Y 103/08004
See application file for complete search history.

(56) References Cited

U.S. PATENT DOCUMENTS

2009/0186358 A1 7/2009 Melville et al.
2010/0021499 A1* 1/2010 Bilsel .................. A61K 39/145
435/236

FOREIGN PATENT DOCUMENTS

| JP | 2006-174786 A | 7/2006 |
|---|---|---|
| WO | WO 2014/022102 A1 | 2/2014 |
| WO | WO 2017/051347 A2 | 3/2017 |

OTHER PUBLICATIONS

Daschner et al. 2001; The mitochondrial isovaleryl-coenzyme A dehydrogenase of *Arabidopsis oxidizes* intermediates of leucine and valine catabolism. Plant Physiology. 126: 601-612.*
Exlended European Search Report for corresponding European Application No. 18887753.4, dated Jan. 18, 2021.
International Preliminary Report on Patentability and English tanslation of the Written Opinion of the International Searching Authority (PCT/IB/326, PCT/IB/373 and PCT/ISA/237) dated Jun. 25, 2020 for Application No. PCT/JP2018/045479.
International Search Report (PCT/ISA/210) dated Mar. 5, 2019 for Application No. PCT/JP2018/045479 with an English translation.
Mohsen et al., "High-level expression of an altered cDNA encoding human isovaleryl-CoA dehydrogenase in *Escherichia coli*", Gene, vol. 160, 1995, pp. 263-267.
Mulukutla et al., "Identification and Control of Novel Growth Inhibitors in Fed-Batch Cultures of Chinese Hamster Ovary Cells", Biotechnolagy and Bioengineering, vol. 114, No. 8, Aug. 2017, pp. 1779-1790.
Urano at al., "Molecular defect of isovalery-CoA dehydrogenase in the skunk mutant of silkworm, Bombyx mori", Febs Journal, vol. 277, 2010, pp. 4452-4463.
Japanese Notice of Reasons for Refusal for corresponding Japanese Application No. 2019-559655, dated Jul. 27, 2021, with an English translation.
Mohsen et al., "High-level expression of an altered cDNA encoding human isovaleryl-CoA dehydrogenase in *Escherichia coli*" Gene, vol. 160, 1995, pp. 263-267, 6 pages total.
Mulukutla et al.,"Idenfication and Control of Novel Growth inhibitors in Fed-Batch Cultures of Chinese Hamster Ovary Cells," Biotechnology and Bioengineering, vol. 114, No. 8, 2017, pp. 1779-1790, 13 pages total.
Urano et al., "Molecular defect of isovaleryl-CoA dehydrogenase in the *skunk* mutant of silkworm, *Bombyx mori*," FEES Journal, vol. 277, 2010, pp. 4452-4463, 13 pages total.

* cited by examiner

Primary Examiner — Karen Cochrane Carlson
(74) Attorney, Agent, or Firm — Birch, Stewart, Kolasch & Birch, LLP

(57) ABSTRACT

An object of the present invention is to provide an animal cell with improved proliferation ability and survival rate, a method for producing the animal cell, and a method for producing a target protein formed of the animal cell. According to the present invention, there is provided an animal cell having a gene encoding a target protein and a foreign gene encoding an isovaleryl-CoA dehydrogenase, in which the isovaleryl-CoA dehydrogenase is overexpressed.

18 Claims, 20 Drawing Sheets
Specification includes a Sequence Listing.

SEQUENCE LISTING

```
<160> NUMBER OF SEQ ID NOS: 8

<210> SEQ ID NO 1
<211> LENGTH: 1269
<212> TYPE: DNA
<213> ORGANISM: human
<220> FEATURE:
<221> NAME/KEY: CDS
<222> LOCATION: (1)..(1269)

<400> SEQUENCE: 1 atg gcg act gcg act cgg ctg ctg ggg tgt cgt gtg gcg agc tgg agg      48
Met Ala Thr Ala Thr Arg Leu Leu Gly Cys Arg Val Ala Ser Trp Arg
1               5                   10                  15 ctg cgg ccg ccg ctt gcc ggc ttc gtt tcc cag cgg gcc cac tcg ctt      96
Leu Arg Pro Pro Leu Ala Gly Phe Val Ser Gln Arg Ala His Ser Leu
                20                  25                  30 ttg ccc gtg gac gat gca atc aat ggg cta agc gag gag cag agg cag     144
Leu Pro Val Asp Asp Ala Ile Asn Gly Leu Ser Glu Glu Gln Arg Gln
            35                  40                  45 ctt cgt cag acc atg gct aag ttc ctt cag gag cac ctg gcc ccc aag     192
Leu Arg Gln Thr Met Ala Lys Phe Leu Gln Glu His Leu Ala Pro Lys
        50                  55                  60 gcc cag gag atc gat cgc agc aat gag ttc aag aac ctg cga gaa ttt     240
Ala Gln Glu Ile Asp Arg Ser Asn Glu Phe Lys Asn Leu Arg Glu Phe
65                  70                  75                  80 tgg aag cag ctg ggg aac ctg ggc gta ttg ggc atc aca gcc cct gtt     288
Trp Lys Gln Leu Gly Asn Leu Gly Val Leu Gly Ile Thr Ala Pro Val
                85                  90                  95 cag tat ggc ggc tcc ggc ctg ggc tac ctg gag cat gtg ctg gtg atg     336
Gln Tyr Gly Gly Ser Gly Leu Gly Tyr Leu Glu His Val Leu Val Met
                100                 105                 110 gag gag ata tcc cga gct tcc gga gca gtg ggg ctc agt tac ggt gcc     384
Glu Glu Ile Ser Arg Ala Ser Gly Ala Val Gly Leu Ser Tyr Gly Ala
            115                 120                 125 cac tcc aac ctc tgc atc aac cag ctt gta cgc aat ggg aat gag gcc     432
His Ser Asn Leu Cys Ile Asn Gln Leu Val Arg Asn Gly Asn Glu Ala
```

```
                     130                 135                 140
cag aaa gag aag tat ctc ccg aag ctg atc agt ggt gag tac atc gga      480
Gln Lys Glu Lys Tyr Leu Pro Lys Leu Ile Ser Gly Glu Tyr Ile Gly
145                 150                 155                 160 gcc ctg gcc atg agt gag ccc aat gca ggc tct gat gtt gtc tct atg      528
Ala Leu Ala Met Ser Glu Pro Asn Ala Gly Ser Asp Val Val Ser Met
                165                 170                 175 aag ctc aaa gcg gaa aag aaa gga aat cac tac atc ctg aat ggc aac      576
Lys Leu Lys Ala Glu Lys Lys Gly Asn His Tyr Ile Leu Asn Gly Asn
            180                 185                 190 aag ttc tgg atc act aat ggc cct gat gct gac gtc ctg att gtc tat      624
Lys Phe Trp Ile Thr Asn Gly Pro Asp Ala Asp Val Leu Ile Val Tyr
        195                 200                 205 gcc aag aca gat ctg gct gct gtg cca gct tct cgg ggc atc aca gcc      672
Ala Lys Thr Asp Leu Ala Ala Val Pro Ala Ser Arg Gly Ile Thr Ala
    210                 215                 220 ttc att gtg gag aag ggt atg cct ggc ttt agc acc tct aag aag ctg      720
Phe Ile Val Glu Lys Gly Met Pro Gly Phe Ser Thr Ser Lys Lys Leu
225                 230                 235                 240 gac aag ctg ggg atg agg ggc tct aac acc tgt gag cta atc ttt gaa      768
Asp Lys Leu Gly Met Arg Gly Ser Asn Thr Cys Glu Leu Ile Phe Glu
                245                 250                 255 gac tgc aag att cct gct gcc aac atc ctg ggc cat gag aat aag ggt      816
Asp Cys Lys Ile Pro Ala Ala Asn Ile Leu Gly His Glu Asn Lys Gly
            260                 265                 270 gtc tac gtg ctg atg agt ggg ctg gac ctg gag cgg ctg gtg ctg gcc      864
Val Tyr Val Leu Met Ser Gly Leu Asp Leu Glu Arg Leu Val Leu Ala
        275                 280                 285 ggg ggg cct ctt ggg ctc atg caa gcg gtc ctg gac cac acc att ccc      912
Gly Gly Pro Leu Gly Leu Met Gln Ala Val Leu Asp His Thr Ile Pro
    290                 295                 300 tac ctg cac gtg agg gaa gcc ttt ggc cag aag atc ggc cac ttc cag      960
Tyr Leu His Val Arg Glu Ala Phe Gly Gln Lys Ile Gly His Phe Gln
305                 310                 315                 320 ttg atg cag ggg aag atg gct gac atg tac acc cgc ctc atg gcg tgt     1008
Leu Met Gln Gly Lys Met Ala Asp Met Tyr Thr Arg Leu Met Ala Cys
                325                 330                 335 cgg cag tat gtc tac aat gtc gcc aag gcc tgc gat gag ggc cat tgc     1056
Arg Gln Tyr Val Tyr Asn Val Ala Lys Ala Cys Asp Glu Gly His Cys
            340                 345                 350 act gct aag gac tgt gca ggt gtg att ctt tac tca gct gag tgt gcc     1104
Thr Ala Lys Asp Cys Ala Gly Val Ile Leu Tyr Ser Ala Glu Cys Ala
        355                 360                 365 aca cag gta gcc ctg gac ggc att cag tgt ttt ggt ggc aat ggc tac     1152
Thr Gln Val Ala Leu Asp Gly Ile Gln Cys Phe Gly Gly Asn Gly Tyr
    370                 375                 380 atc aat gac ttt ccc atg ggc cgc ttt ctt cga gat gcc aag ctg tat     1200
Ile Asn Asp Phe Pro Met Gly Arg Phe Leu Arg Asp Ala Lys Leu Tyr
385                 390                 395                 400 gag ata ggg gct ggg acc agc gag gtg agg cgg ctg gtc atc ggc aga     1248
Glu Ile Gly Ala Gly Thr Ser Glu Val Arg Arg Leu Val Ile Gly Arg
                405                 410                 415 gcc ttc aat gca gac ttt cac                                         1269
Ala Phe Asn Ala Asp Phe His
            420

<210> SEQ ID NO 2
<211> LENGTH: 423
<212> TYPE: PRT
<213> ORGANISM: human
```

<400> SEQUENCE: 2

```
Met Ala Thr Ala Thr Arg Leu Leu Gly Cys Arg Val Ala Ser Trp Arg
1               5                   10                  15

Leu Arg Pro Pro Leu Ala Gly Phe Val Ser Gln Arg Ala His Ser Leu
            20                  25                  30

Leu Pro Val Asp Asp Ala Ile Asn Gly Leu Ser Glu Glu Gln Arg Gln
        35                  40                  45

Leu Arg Gln Thr Met Ala Lys Phe Leu Gln Glu His Leu Ala Pro Lys
50                  55                  60

Ala Gln Glu Ile Asp Arg Ser Asn Glu Phe Lys Asn Leu Arg Glu Phe
65              70                  75                  80

Trp Lys Gln Leu Gly Asn Leu Gly Val Leu Gly Ile Thr Ala Pro Val
                85                  90                  95

Gln Tyr Gly Gly Ser Gly Leu Gly Tyr Leu Glu His Val Leu Val Met
            100                 105                 110

Glu Glu Ile Ser Arg Ala Ser Gly Ala Val Gly Leu Ser Tyr Gly Ala
        115                 120                 125

His Ser Asn Leu Cys Ile Asn Gln Leu Val Arg Asn Gly Asn Glu Ala
130                 135                 140

Gln Lys Glu Lys Tyr Leu Pro Lys Leu Ile Ser Gly Glu Tyr Ile Gly
145                 150                 155                 160

Ala Leu Ala Met Ser Glu Pro Asn Ala Gly Ser Asp Val Val Ser Met
                165                 170                 175

Lys Leu Lys Ala Glu Lys Lys Gly Asn His Tyr Ile Leu Asn Gly Asn
            180                 185                 190

Lys Phe Trp Ile Thr Asn Gly Pro Asp Ala Asp Val Leu Ile Val Tyr
        195                 200                 205

Ala Lys Thr Asp Leu Ala Ala Val Pro Ala Ser Arg Gly Ile Thr Ala
210                 215                 220

Phe Ile Val Glu Lys Gly Met Pro Gly Phe Ser Thr Ser Lys Lys Leu
225                 230                 235                 240

Asp Lys Leu Gly Met Arg Gly Ser Asn Thr Cys Glu Leu Ile Phe Glu
                245                 250                 255

Asp Cys Lys Ile Pro Ala Ala Asn Ile Leu Gly His Glu Asn Lys Gly
            260                 265                 270

Val Tyr Val Leu Met Ser Gly Leu Asp Leu Glu Arg Leu Val Leu Ala
        275                 280                 285

Gly Gly Pro Leu Gly Leu Met Gln Ala Val Leu Asp His Thr Ile Pro
290                 295                 300

Tyr Leu His Val Arg Glu Ala Phe Gly Gln Lys Ile Gly His Phe Gln
305                 310                 315                 320

Leu Met Gln Gly Lys Met Ala Asp Met Tyr Thr Arg Leu Met Ala Cys
                325                 330                 335

Arg Gln Tyr Val Tyr Asn Val Ala Lys Ala Cys Asp Glu Gly His Cys
            340                 345                 350

Thr Ala Lys Asp Cys Ala Gly Val Ile Leu Tyr Ser Ala Glu Cys Ala
        355                 360                 365

Thr Gln Val Ala Leu Asp Gly Ile Gln Cys Phe Gly Gly Asn Gly Tyr
370                 375                 380

Ile Asn Asp Phe Pro Met Gly Arg Phe Leu Arg Asp Ala Lys Leu Tyr
385                 390                 395                 400

Glu Ile Gly Ala Gly Thr Ser Glu Val Arg Arg Leu Val Ile Gly Arg
```

Ala Phe Asn Ala Asp Phe His
            420

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 3
agttgatgca ggggaagatg                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4
tcatacagct tggcatctcg                                                   20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
agctgagagg gaaattgtgc g                                                 21

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6
gcaacggaac cgctcatt                                                     18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
tcgaggattt ggaaaaggtg                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

```
<400> SEQUENCE: 8
aatccagcag gtcagcaaag                                        20
```

ANIMAL CELL, METHOD FOR PRODUCING ANIMAL CELL, AND METHOD FOR PRODUCING TARGET PROTEIN

CROSS-REFERENCE TO RELATED APPLICATIONS

This application is a Continuation of PCT International Application No. PCT/JP2018/045479 filed on Dec. 11, 2018, which claims priority under 35 U.S.C § 119(a) to Japanese Patent Application No. 2017-236641 filed on Dec. 11, 2017. Each of the above application(s) is hereby expressly incorporated by reference, in its entirety, into the present application.

BACKGROUND OF THE INVENTION

1. Field of the Invention

The present invention relates to animal cells that express a target protein. The present invention relates to a method for producing the above-mentioned animal cells, and a method for producing a target protein formed of the above-mentioned animal cells.

2. Description of the Related Art

In producing biopharmaceuticals such as antibodies, fed-batch culture, which improves a state of cells by adding nutrients to a culture solution, is often used to improve the productivity of antibodies. In addition, in producing biopharmaceuticals such as antibodies, a perfusion culture method, in which a culture solution is continuously filtered and discharged while a fresh medium containing nutrients is continuously fed to a culture tank, is often used to improve the productivity of antibodies.

Organic acids are exemplified as waste products that reduce proliferative properties and viability of cells. Among these, an isovaleric acid, which has particularly high inhibitory properties, is an organic acid generated as an intermediate product due to the metabolism of leucine, and is generally known as a substance generating an offensive odor. In a metabolic pathway of leucine, leucine is enzymatically converted intracellularly into an isovaleryl-CoA (3-methylbutanoyl-CoA). The isovaleryl-CoA is converted into a 3-methylbut-2-enoyl-CoA by an isovaleryl-CoA dehydrogenase (also abbreviated as IVD), which is a downstream enzyme thereof. In a case where the IVD activity is reduced or deficient, isovaleryl-CoA which is an intermediate product is non-enzymatically decomposed and an isovaleric acid is generated (FIG. 1). In patients with genetically mutated or deficient IVD genes, isovaleric acids are accumulated and cranial neuropathy is caused (isovaleric acidemia).

Biotechnology and Bioengineering, vol. 114, 2017, 1779-1790 discloses that in Chinese hamster ovary (CHO) cells, an isovaleric acid secreted from the cells acts on proliferation inhibition. In Biotechnology and Bioengineering, vol. 114, 2017, 1779-1790, a secretion amount of an isovaleric acid is reduced and proliferative properties are improved by performing a fed-batch culture using a low leucine medium.

JP2006-174786A discloses that a production amount of an isovaleric acid is reduced and a food with less unpleasant odor is produced by introducing an isovaleryl-CoA dehydrogenase gene into a microorganism.

WO2017/051347A discloses that CHO cells are cultured in a leucine-reduced medium.

SUMMARY OF THE INVENTION

In the fed-batch culture, it is possible to perform a cell culture for a longer period and at a higher concentration compared to a case where nutrients are not additionally added, but there is a problem in that viability is degraded in the latter half of the culture due to when no additional nutrients are added, but viability is reduced in the latter half of the culture due to accumulation of waste products secreted from cells. In addition, there is a problem in that in order to perform culture at high density in the perfusion culture method, the cost of the culture is increased since a culture is performed while exchanging a medium in an amount of 1 to 3 times the culture volume per day to discharge waste products out of the system, in addition to the supply of nutrients.

An object of the present invention is to provide an animal cell with improved proliferation ability and survival rate. Another object of the present invention is to provide a method for producing the animal cell and a method for producing a target protein formed of the animal cell.

The present inventors have conducted intensive studies to solve the above-mentioned problems, and as a result, the present inventors found that it is possible to reduce production of an isovaleric acid and a butyric acid by forcibly expressing a gene encoding enzyme isovaleryl-CoA dehydrogenase, which promotes the downstream reaction of the isovaleric acid metabolic pathway, in CHO cells. In addition, the present inventors have demonstrated that as the above result, the state of the cells is improved, and the proliferative properties and viability are improved. The present invention was completed based on the above findings.

That is, according to the present invention, the following inventions are provided.

<1> An animal cell that has a gene encoding a target protein and a foreign gene encoding an isovaleryl-CoA dehydrogenase, and overexpresses the isovaleryl-CoA dehydrogenase.

<2> The animal cell according to <1>, in which the foreign gene encoding an isovaleryl-CoA dehydrogenase is linked to a promoter.

<3> The animal cell according to <1> or <2>, in which the animal cell is a CHO cell.

<4> The animal cell according to any one of <1> to <3>, in which an expression level of the isovaleryl-CoA dehydrogenase is three times or more that of the animal cell not having a foreign gene encoding an isovaleryl-CoA dehydrogenase.

<5> The animal cell according to any one of <1> to <4>, in which the gene encoding a target protein and the foreign gene encoding an isovaleryl-CoA dehydrogenase are present on the same expression vector.

<6> A method for producing the animal cell according to any one of <1> to <5>, the method comprising: a step of introducing the gene encoding a target protein and the foreign gene encoding an isovaleryl-CoA dehydrogenase into the animal cell.

<7> The method according to <6>, in which the step of introducing the foreign gene encoding an isovaleryl-CoA dehydrogenase is performed by electroporation.

<8> The method according to <6> or <7>, introducing the gene encoding a target protein and the foreign gene encoding an isovaleryl-CoA dehydrogenase, using the same expression vector including the gene encoding a target protein and the foreign gene encoding an isovaleryl-CoA dehydrogenase.

<9> A method for producing a target protein, comprising culturing the animal cell according to any one of <1> to <5>.

<10> The method according to <9>, in which a culture of the animal cell is a fed-batch culture or a batch culture.

<11> The method according to <10>, in which a seeded cell density of a cell culture is $0.2\times10^6$ cells/mL to $5\times10^6$ cells/mL.

<12> The method according to <10> or <11>, in which a viable cell rate during a culture period is 60% or more over the entire period.

<13> The method according to any one of <10> to <12>, in which a maximum concentration of an isovaleric acid in a culture solution throughout the culture period is 3,000 μmol/L or less.

<14> The method according to any one of <10> to <13>, in which a secretion amount of the isovaleric acid per cell throughout the culture period is 30 fmol/cell/day or less.

<15> The method according to any one of <10> to <14>, in which a maximum concentration of a butyric acid in the culture solution throughout the culture period is 3,000 μmol/L or less.

<16> The method according to any one of <10> to <15>, in which a secretion amount of the butyric acid per cell throughout the culture period is 30 fmol/cell/day or less.

<17> The method according to <9>, in which a culture of the animal cell is a perfusion culture.

<18> The method according to <17>, in which the seeded cell density of the cell culture is $0.2\times10^6$ cells/mL to $3\times10^7$ cells/mL.

<19> The method according to <17> or <18>, in which the viable cell rate during the culture period is 90% or more over the entire period.

<20> The method according to any one of <17> to <19>, in which a concentration of the isovaleric acid in the culture solution is 3,000 μmol/L or less.

<21> The method according to any one of <17> to <20>, in which a secretion amount of the isovaleric acid per cell is 30 fmol/cell/day or less.

<22> The method according to any one of <17> to <21>, in which a concentration of the butyric acid in the culture solution throughout the culture period is 3,000 μmol/L or less.

<23> The method according to any one of <17> to <22>, in which a secretion amount of the butyric acid per cell throughout the culture period is 30 fmol/cell/day or less.

The animal cell of the present invention has a high proliferation ability and a high survival rate. According to the animal cell of the present invention, it is possible to produce a target protein with high productivity.

DESCRIPTION OF THE PREFERRED EMBODIMENTS

Figure 1:
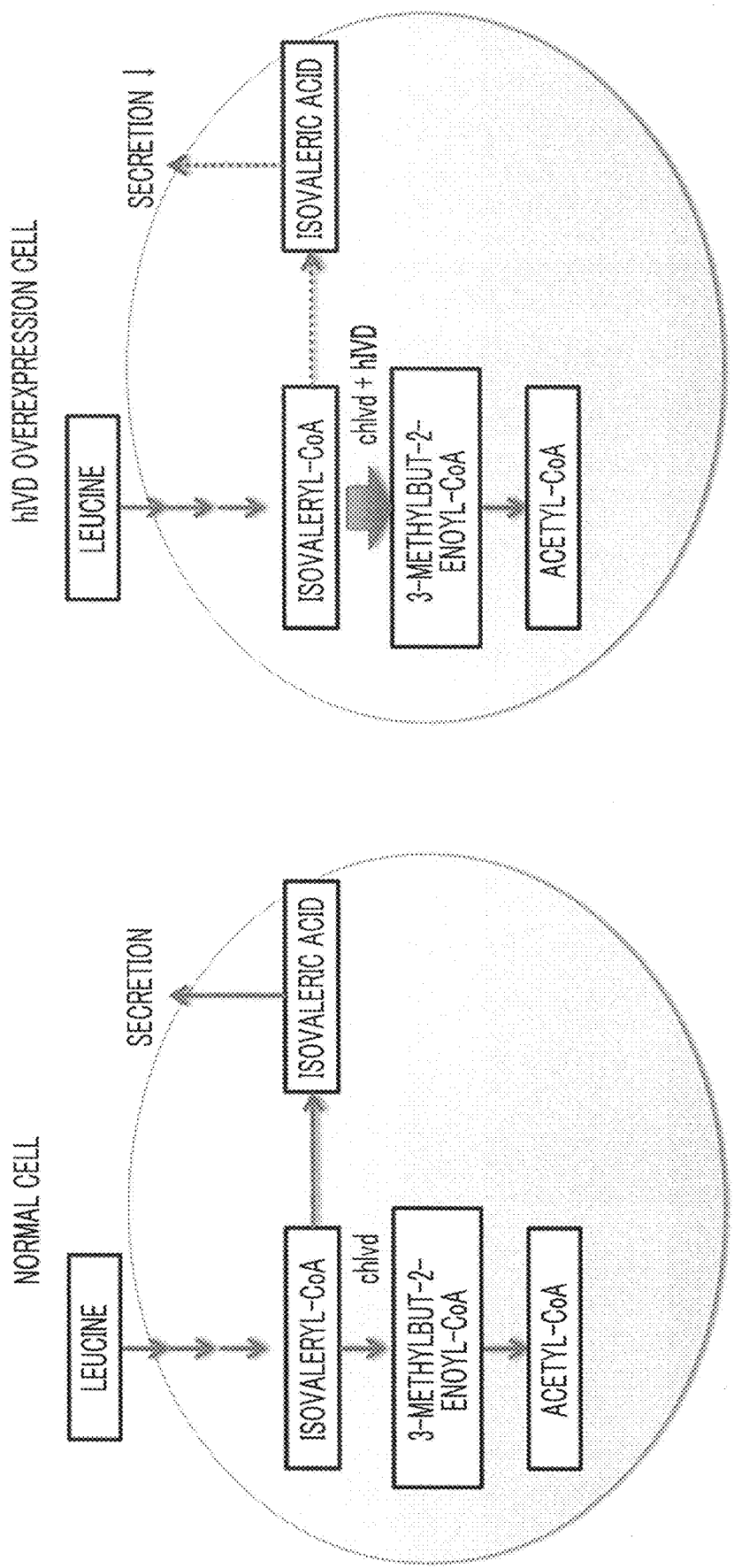
FIG. 1 illustrates a metabolic pathway of leucine in cells. chIvd indicates a CHO cell endogenous isovaleryl-CoA dehydrogenase, and hIVD indicates an exogenous human isovaleryl-CoA dehydrogenase.

Hereinafter, embodiments for carrying out the present invention will be described in detail.

In the present specification, a numerical value range indicated by using "to" means a range including numerical values described before and after the "to" as a minimum value and a maximum value, respectively.

[Animal Cells]

An animal cell of the present invention is an animal cell that includes a gene encoding a target protein and a foreign gene encoding a isovaleryl-CoA dehydrogenase, and overexpresses the isovaleryl-CoA dehydrogenase.

Similar to many other low-molecular organic acids, the isovaleric acid is known to stop a cell cycle by inhibiting a histone deacetylase and thereby to inhibit proliferation. In a case where CHO cells are cultured, the isovaleric acids are accumulated for the above-described reason, so that proliferation of the cells is stopped in a later period of culture and the survival rate is reduced. Due to the reduced survival rate, a production amount of proteins per cell is reduced.

In Biotechnology and Bioengineering, vol. 114, 2017, 1779-1790, a secretion amount of the isovaleric acid is reduced by performing a fed-batch culture using a low leucine medium. However, the method described in Biotechnology and Bioengineering, vol. 114, 2017, 1779-1790 lacks versatility since it is not possible to use a leucine reduction formulation in a commercially available medium. In addition, in Biotechnology and Bioengineering, vol. 114, 2017, 1779-1790, although proliferative properties of cells are improved, the viability in the latter half of the culture cannot be maintained, and the IgG production amount (Qp) per cell is reduced. Therefore, there is no change in a total antibody production amount. On the contrary, in the present invention, by controlling cells themselves, it is possible to suppress secretion of the isovaleric acid regardless of the kind of the medium. In addition, in the present invention, the cells of the present invention can maintain high viability in the latter half of the culture, and can increase the total antibody production by improving the proliferative properties while maintaining the antibody production per cell.

In JP2006-174786A, reduction of isovaleric acids is aimed at reducing the offensive odor of food products, and there is no mention in relation to the cell proliferation inhibitory properties of the isovaleric acids themselves. In addition, a subject of JP2006-174786A is a microorganism, and an animal cell is not a subject and does not relate to production of a target protein. On the contrary, in the present invention, it is possible to promote proliferation of CHO cells by reducing the production of the isovaleric acid, and it is possible to efficiently produce the target protein.

In the present invention, an addition amount of leucine is not reduced, and an isovaleryl-CoA dehydrogenase gene is introduced into an animal cell for the purpose of activating a metabolic pathway of leucine and resolving accumulation of the isovaleryl-CoA which is an intermediate product. Cells highly expressing the isovaleryl-CoA dehydrogenase can suppress a secretion amount of the isovaleric acid regardless of the kind of the medium by rapidly exchanging isovaleryl-CoA with 3-methylbut-2-enoyl-CoA. As described above, it is possible to perform a culture with high proliferative properties and viability using cells of the present invention by providing cells with low secretion of the isovaleric acid regardless of the kind of the medium. In particular, it is possible to maintain high viability of cells in the later period of culture (the 10th day or later after the start of culture) in which waste products easily accumulate. In the present invention, it is possible to increase the productivity of protein per cell and to increase the total production amount of protein by a general culture method by maintaining high viability. Further, as a secondary effect, it can be expected to decrease a host-derived protein and a DNA mixed amount, which is problematic at a time of protein purification which is a downstream step, by reducing dead cells. Furthermore, in the cells of the present invention, the secretion amount of the butyric acid, which is known to have a proliferation inhibitory activity similar to the isovaleric acid, is suppressed. Since the isovaleryl-CoA dehydrogenase is not directly involved in the metabolic pathway of butyric acid production, it is an unexpected result that the secretion amount of the butyric acid in the animal cells of the present invention can be decreased.

In addition, it is known that while the isovaleric acid and the butyric acid suppress cell division by inhibiting a histone deacetylase (HDAC), the isovaleric acid and the butyric acid they improve the productivity of the target protein by activating gene expression, that is, increase the production amount of antibodies per cell (Qp). Therefore, it was expected that in a case where the secretion amount of the isovaleric acid and the butyric acid is decreased, the production amount of antibodies per cell (Qp) is also decreased. However, in the present invention, although the isovaleric acid and the butyric acid were decreased by high expression of an isovaleryl-CoA dehydrogenase, the productivity of the target protein (the production amount of antibodies per cell (Qp)) was not decreased, and it was possible to improve the production amount of the target protein by improving the proliferation rate of cells.

In addition, effects of the present invention can be exhibited in both of the fed-batch culture, the batch culture, and the perfusion culture. In the perfusion culture, accumulation of the waste products becomes a problem during low perfusion ratio culture, but a culture is possible while maintaining the proliferative properties and the viability by using the animal cells of the present invention. In addition, since it is possible to suppress secretion and accumulation of the waste products, a high perfusion ratio is not necessary even at a time of a high-density culture using a perfusion culture. Therefore, it is possible to perform a culture while maintaining the quality even in a low perfusion ratio state. In addition, since a culture is possible without generating cell debris due to high viability, it becomes possible to avoid clogging of the cells can be cultured without generating cell debris due to high viability, clogging of a separation membrane used during the perfusion culture.

<Target Protein>

In the present invention, the kind of the target protein is not particularly limited, and examples thereof include a recombinant polypeptide chain, a recombinant secreted polypeptide chain, an antigen-binding protein, a human antibody, a humanized antibody, a chimeric antibody, a mouse antibody, a bispecific antibody, and an Fc fusion protein, a fragmented immune immunoglobulin, and a single chain antibody (scFv). The target protein is preferably a human antibody, a humanized antibody, a chimeric antibody, or a mouse antibody. Examples of the fragmented immune immunoglobulin include Fab, $F(ab')_2$, Fv, and the like. The class of the antibody is also not particularly limited, and may be any one class of IgG such as IgG1, IgG2, IgG3, and IgG4, IgA, IgD, IgE, or IgM, but in a case of being used in combination with a medicine, IgG and IgM are preferable.

Human antibodies include all antibodies having one or a plurality of variable and constant domains introduced from human immunoglobulin sequences. In one embodiment, all of the variable and constant domains are introduced from human immunoglobulin sequences (complete human antibodies).

The humanized antibody has a sequence different from a sequence of an antibody introduced from a non-human species by one or a plurality of amino acid substitution, deletion, and/or addition, so that the there is a low possibility for the humanized antibody to induce an immune response, and/or so that induction of a severe immune response is reduced, compared to the non-human species antibody, in a case of being administered to a human subject. In one embodiment, specific amino acids in a framework of heavy chains and/or light chains and constant domains of a non-human species antibody are mutated to produce a humanized antibody. In another embodiment, the constant domains from human antibodies are fused to variable domains of a non-human species.

The chimeric antibody is an antibody in which variable domains and constant domains having different origins from each other are linked. For example, an antibody consisting of variable domains of heavy chains and light chains of a mouse antibody and the constant domains of heavy chains and light chains of a human antibody is a mouse/human heterologous chimeric antibody. It is possible to prepare a recombinant vector expressing a chimeric antibody by linking a DNA encoding the variable domains of a mouse antibody and a DNA encoding the constant domains of a human antibody, and incorporating thereof into an expression vector. It is possible to obtain a chimeric antibody produced during the culture by culturing a recombinant cell transformed with the vector and expressing the incorporated DNA.

A bispecific antibody is an antibody that recognizes two different antigenic specificities and are prepared by a chemical method or cell fusion. As a method for producing a bispecific antibody, a method of preparing a bispecific antibody by binding two immunoglobulin molecules by using a cross-linking agent such as N-succinimidyl 3-(2-pyridyldithiol) propionate or S-acetylmercaptosuccinic acid anhydride, a method of preparing a bispecific antibody by binding Fab fragments of immunoglobulin molecules, and the like have been reported.

An Fc fusion protein indicates a protein having an Fc domain and includes an antibody. Fab is a monovalent fragment having $V_L$, $V_H$, $C_L$ and $C_H1$ domains.

F(ab')$_2$ is a bivalent fragment having two Fab fragments bound by a disulfide cross-linking at a hinge domain.

The Fv fragment has the single arm $V_L$ and $V_H$ domains of an antibody.

Single-chain antibodies (scFv) are antibodies in which the $V_L$ and $V_H$ domains are joined via a linker (for example, a synthetic sequence of an amino acid residue) to form a continuous protein chain, in which the linker is long enough to fold the protein chain on itself to form a monovalent antigen binding site.

A gene encoding a target protein can be obtained by a method known to those skilled in the art. In a case where the target protein is an antibody, it is possible to use a DNA encoding the L chain and a DNA encoding the H chain of the antibody.

It is possible to prepare the DNA encoding the L chain and the DNA encoding the H chain of the antibody as follows. An mRNA is extracted from a hybridoma, a cell, a phage, a ribosome, and the like having a gene that expresses the antibody. A cDNA is prepared by a reverse transcription reaction using a reverse transcriptase due to the mRNA. The L chain gene or the H chain gene is amplified by PCR using a primer and a cDNA having a base sequence complementary to the L chain gene or the H chain gene, and each gene is obtained by binding to a cloning plasmid.

It is possible to prepare the DNA encoding the L chain fragment and the DNA encoding the H chain fragment of the antibody as follows. An mRNA is extracted from a hybridoma, a cell, a phage, a ribosome, and the like having a gene that expresses the antibody. A cDNA is prepared by a reverse transcription reaction using a reverse transcriptase due to the mRNA. The L chain gene fragment or the H chain gene fragment is amplified by PCR using a primer and a cDNA having a base sequence complementary to the L chain gene fragment or the H chain gene fragment, and each gene fragment is obtained by binding to a cloning plasmid.

<Isovaleryl-CoA Dehydrogenase and Isovaleryl-CoA Dehydrogenase Gene>

In the present invention, the origin of the isovaleryl-CoA dehydrogenase is not particularly limited, and it is possible to use a foreign gene encoding an isovaleryl-CoA dehydrogenase derived from mammals such as human, monkey, mouse, rat, and hamster. In the present invention, the foreign gene refers to a gene introduced into an animal cell from outside. In addition, even in a case where an endogenous gene is amplified to introduce a gene, it is regarded as a foreign gene.

A base sequence and an amino acid sequence of the human isovaleryl-CoA dehydrogenase are shown in SEQ ID NOs: 1 and 2 in the sequence listing.

As foreign genes encoding an isovaleryl-CoA dehydrogenase, (1) a gene encoding a protein consisting of an amino acid sequence of SEQ ID NO: 2;

(2) a gene consisting of an amino acid sequence in which one or several amino acids are deleted, substituted, or added in the amino acid sequence of SEQ ID NO: 2, and encoding a protein having isovaleryl-CoA dehydrogenase activity; or (3) a gene consisting of an amino acid sequence having 85% or more (more preferably 90% or more, particularly preferably 95% or more, most preferably 98% or more) sequence identity with the amino acid sequence of SEQ ID NO: 2, and encoding a protein having isovaleryl-CoA dehydrogenase activity; can be used.

As the foreign gene encoding an isovaleryl-CoA dehydrogenase, (4) a gene consisting of a base sequence of SEQ ID NO: 1;

(5) a gene consisting of a base sequence in which one or several bases are deleted, substituted or added in the base sequence of SEQ ID NO: 1, and encoding a protein having isovaleryl-CoA dehydrogenase activity; or (6) a gene consisting of a base sequence that hybridizes under stringent conditions to a complementary sequence to the base sequence of SEQ ID NO: 1 and encoding a protein having isovaleryl-CoA dehydrogenase activity; can also be used.

"One or several" in the "amino acid sequence in which one or several amino acids are deleted, substituted or added" means preferably 1 to 20, more preferably 1 to 10, further more preferably 1 to 5, and particularly preferably 1 to 3.

The sequence identity in the present invention indicates a value calculated by the following formula.

% Sequence identity=[(number of identical residues)/ (longer alignment length)]×100

The sequence identity between two amino acid sequences can be determined by any method known to those skilled in the art, and can be determined using the basic local alignment search tool (BLAST) program (J. Mol. Biol. 215: 403-410, 1990) and the like. The "longer alignment length" of the denominator means that in a case where two alignments are compared, the longer alignment length is used as the denominator.

"One or several" in the "base sequence in which one or several bases are deleted, substituted or added" means preferably 1 to 20, more preferably 1 to 10, further more preferably 1 to 5, and particularly preferably 1 to 3.

"Under the stringent conditions" in "hybridizes under stringent conditions" means hybridizing under moderately or highly stringent conditions, which can be recognized by those skilled in the art. Examples of the moderately stringent conditions include conditions described in Sambrook et al., Molecular Cloning: A Laboratory Manual, Third Edition, Vol. 1, 7. 42-7.45 Cold Spring Harbor Laboratory Press, 2001. Examples of the moderately stringent conditions include a hybridization conditions of 5×SSC, 0.5% SDS, a pre-wash solution of 1.0 mmol/L EDTA (pH 8.0), approximately 50% formamide at approximately 40° C. to 50° C., 2×SSC to 6×SSC (or other similar hybridization solutions such as Stark's solution in approximately 50% formamide at approximately 42° C.) in a nitrocellulose filter, and washing conditions of approximately 60° C., 0.5×SSC, AND 0.1% SDS. Highly stringent conditions can also be easily determined by those skilled in the art, and examples thereof include hybridization and/or washing at a higher temperature and/or a lower salt concentration than the above-described moderately stringent conditions. For example, the above-described hybridization conditions and washing at 68° C., 0.2×SSC, and 0.1% SDS can be exemplified. Here, the composition of 1×SSC is 150 mmol/L NaCl, 15 mmol/L sodium citrate, and pH 7.4. SDS is sodium dodecyl sulfate, and EDTA is ethylene diamine tetraacetic acid.

Information on the amino acid sequence and the base sequence of a non-human isovaleryl-CoA dehydrogenase is shown below. The numbers below indicate Gene No. of the National Center for Biotechnology Information (NCBI).

ID: 24513 rat
ID: 56357 mouse
ID: 368775 zebrafish
ID: 510440 cow
ID: 423011 chicken
ID: 702867 Rhesus monkey
ID: 100856316 dog
ID: 100156047 pig
ID: 100759847 Chinese hamster In the case of the non-human isovaleryl-CoA dehydrogenase, similar to the case of a human isovaleryl-CoA dehydrogenase, (2A) a gene consisting of an amino acid sequence in which one or several amino acids are deleted, substituted or added in a predetermined amino acid sequence, and encoding a protein having isovaleryl-CoA dehydrogenase activity;

(3A) a gene consisting of an amino acid sequence having 85% or more (more preferably 90% or more, particularly preferably 95% or more, and most preferably 98% or more) sequence identity with a predetermined amino acid sequence, and encoding a protein having isovaleryl-CoA dehydrogenase activity;

(5A) a gene consisting of a base sequence in which one or several bases are deleted, substituted or added in a predetermined base sequence and encoding a protein having isovaleryl-CoA dehydrogenase activity; or (6A) a gene consisting of a base sequence that hybridizes under stringent conditions to a complementary sequence to a predetermined base sequence, and encoding a protein having isovaleryl-CoA dehydrogenase activity; may be used.

A foreign gene encoding isovaleryl-CoA dehydrogenase is preferably linked to a promoter.

The promoter is not particularly limited as long as it can function in animal cells of a host and express an isovaleryl-CoA dehydrogenase. The promoter is preferably CMV promoter (cytomegalovirus promoter), EF1α promoter (promoter of human polypeptide chain elongation factor gene), SV40 promoter (Simian Virus 40 promoter), β-actin promoter, MMLV-LTR promoter (promoter of long terminal repeat of moloney murine leukemia virus), or mouse β-globin promoter, and the CMV promoter is more preferable.

In the animal cells of the present invention, the isovaleryl-CoA dehydrogenase is overexpressed. Overexpression means that expression of a certain gene exceeds a normal expression level in a host. It is possible to obtain an animal cell overexpressing an isovaleryl-CoA dehydrogenase by introducing a foreign gene of the isovaleryl-CoA dehydrogenase into a host and expressing the foreign gene in the host.

The expression level of the isovaleryl-CoA dehydrogenase in the animal cells of the present invention is preferably 3 times or more, more preferably 3.5 times or more, and further more preferably 4 times or more, further more preferably 4.5 times or more, further more preferably 5 times or more, and particularly preferably 5.5 times or more that of animal cells not having a foreign gene encoding an isovaleryl-CoA dehydrogenase. There may be no upper limit, but it may be 30,000 times or less, or may be 10,000 times or less.

The expression level of the isovaleryl-CoA dehydrogenase can be prepared by RT-PCR method (reverse transcription-polymerase chain reaction) and the like. The expression level of the isovaleryl-CoA dehydrogenase is preferably performed by reverse transcription of mRNA and real-time PCR. The expression level of the isovaleryl-CoA dehydrogenase is preferably a relative expression level calculated by normalization. Normalization can be performed, for example, by comparative quantification using the expression level of a housekeeping gene such as β-actin or HPRT1 as an endogenous control.

<Animal Cells>

The cells in the present invention are not particularly limited as long as the cells are animal cells. Examples of the animal cells include Chinese hamster ovary (CHO) cells, BHK cells, 293 cells, myeloma cells (such as NS0 cells), PerC6 cells, SP2/0 cells, hybridoma cells, COS cells, 3T3 cells, HeLa cells, Vero cells, MDCK cells, PC12 cells, and WI38 cells. Among these, CHO cells, BHK cells, 293 cells, myeloma cells (such as NS0 cells), PerC6 cells, SP2/0 cells, and hybridoma cells are particularly preferable, and CHO cells are more preferable. The CHO cells are widely used for production of recombinant proteins such as cytokines, coagulation factors, and antibodies. It is preferable to use CHO cells deficient in dihydrofolate reductase (DHFR), and as DHFR-deficient CHO cells, for example, CHO-DG44 can be used.

In the animal cells of the present invention, a gene encoding a target protein and a foreign gene encoding an isovaleryl-CoA dehydrogenase may be present on the same expression vector, or may be present on different expression vectors. The gene encoding a target protein and the foreign gene encoding an isovaleryl-CoA dehydrogenase are preferably present on the same expression vector. It is considered that as the gene encoding a target protein and the foreign gene encoding an isovaleryl-CoA dehydrogenase are present on the same expression vector, the isovaleryl-CoA dehydrogenase exhibits proliferation action by suppressing a proliferation inhibitory substance called an isovaleric acid, and cells carrying isovaleryl-CoA dehydrogenase genes easily proliferate. It is considered that a synergistic effect (positive selection) is obtained by allowing a gene encoding a target protein to be expressed to be present on an expression vector having an isovaleryl-CoA dehydrogenase gene. In addition, by mounting a gene encoding a target protein and a foreign gene encoding an isovaleryl-CoA dehydrogenase on the same expression vector, a ratio of the number of the above genes becomes 1:1. As an introduction ratio of the foreign gene encoding an isovaleryl-CoA dehydrogenase and an expression efficiency of the target protein are correlated to each other, there is a possibility that the effect of the present invention is exhibited. It is expected that the higher the expression of the isovaleryl-CoA dehydrogenase, the higher the expression of the target protein.

[Method for Producing Animal Cells]

According to the present invention, there is provided a method for producing an animal cell of the present invention, comprising a step of introducing a gene encoding a target protein and a foreign gene encoding an isovaleryl-CoA dehydrogenase into animal cells.

It is preferable that the gene encoding a target protein and the foreign gene encoding an isovaleryl-CoA dehydrogenase are each incorporated into a vector and introduced into a host animal cell.

As the vector that can be used to introduce a gene into a host, it is possible to use a mammalian-derived expression vector. Examples thereof include pCMV6-Entry (manufactured by OriGene Corporation), pcDNA3 (manufactured by Invitrogen Corporation), pEGF-BOS (Nucleic Acids. Res. 1990, 18 (17), p5322), pEF, pCDM8 (manufactured by Funakoshi Corporation), INPEP4 (manufactured by Biogen-IDEC Corporation), and the like, but are not particularly limited thereto.

In addition, it is known that mRNA having poly A is stable in cells. The gene encoding a target protein and the foreign gene encoding an isovaleryl-CoA dehydrogenase may have poly A signals necessary for adding poly A to the gene, for example, mouse β-globin poly A signal, bovine growth hormone poly A signal, SV40 poly A signal, and the like.

The method for introducing a gene encoding a target protein and a foreign gene encoding an isovaleryl-CoA dehydrogenase into animal cells is not particularly limited, and can be performed by a method known to those skilled in the art. For example, it is possible to perform electroporation, lipofection, a calcium phosphate method, a DEAE dextran method, a method using cationic liposome DOTAP (manufactured by Roche Life Science Corporation), or a method using a virus vector. Among these, electroporation is preferable.

In a case where a gene is introduced into an animal cell, the gene is introduced into only some of the cells subjected to gene introduction, depending on the kind of the expression vector used and the gene introduction method. In order to identify and select cells into which the gene has been introduced, for example, a gene encoding a selectable marker for resistance to antibiotics may be introduced into the host cell along with the target gene. Preferable selectable markers include those conferring resistance to drugs, such as G418, hygromycin, and methotrexate.

As described above in the present specification, in the present invention, it is preferable to introduce a gene encoding a target protein and a foreign gene encoding an isovaleryl-CoA dehydrogenase using the same expression vector containing a gene encoding a target protein and a foreign gene encoding an isovaleryl-CoA dehydrogenase.

In the cells of the present invention, the gene encoding a target protein may be expressed in a transient expression system, or may be expressed in a constant expression system, but may be preferably expressed in the constant expression system.

In the cells of the present invention, the foreign gene encoding an isovaleryl-CoA dehydrogenase may be expressed in the transient expression system, or may be expressed in the constant expression system, but may be preferably expressed in the constant expression system.

The transient expression system is a system in which a cyclic plasmid is incorporated into cells and expressed by a calcium phosphate method, an electroporation method, a lipofection method, and the like. A gene encoding a target protein and a foreign gene encoding an isovaleryl-CoA dehydrogenase often exist outside the chromosome.

The constant expression system is a system in which a cyclic plasmid or a linear plasmid created by restriction enzyme treatment is incorporated into cells by a calcium phosphate method, an electroporation method, a lipofection method, and the like, and a part thereof is inserted into a cell genome to express a target protein. It is possible to maintain expression of the gene encoding a target protein and the foreign gene encoding an isovaleryl-CoA dehydrogenase for a long period of time. In addition, drug selection is possible by introduction of a drug resistant gene into a plasmid, and it is possible for the gene encoding a target protein and the foreign gene encoding an isovaleryl-CoA dehydrogenase to efficiently select the cells maintained on chromosomes.

[Method for Producing Target Protein]

According to the present invention, there is provided a method for producing a target protein, comprising culturing an animal cell of the present invention.

It is possible to produce a target protein by culturing the animal cell of the present invention. A culture can be performed according to a known method.

As a medium used for culturing animal cells of the present invention, a medium used for culturing normal animal cells can be used. For example, an OptiCHO (Life Technologies Corporation, 12681011) medium, a Dulbecco's modified eagle medium (DMEM), an eagle's minimum essential medium (MEM), an RPMI-1640 medium, an RPMI-1641 medium, a F-12K medium, a Ham F12 medium, an Iscob's modified method Dulbecco's medium (IMDM), a McCoy's 5A medium, a Leibovitz L-15 medium, and an EX-CELL™ 300 series (JRH Biosciences), a CHO-S-SFMII (Invitrogen Corporation), a CHO-SF (Sigma-Aldrich), a CD-CHO (Invitrogen Corporation), an IS CHO-V (Irvine Scientific Corporation), a PF-ACF-CHO (Sigma-Aldrich Corporation), and like.

Serum such as fetal calf serum (FCS) may be added to the medium, may be more preferably cultured on a serum-free medium, and may be most preferably cultured on a synthetic medium.

The medium may be supplemented with additional components such as amino acids, salts, sugars, vitamins, hormones, proliferation factors, buffers, antibiotics, lipids, trace elements, and hydrolysates of plant proteins.

The pH of the medium varies depending on the cells to be cultured, but is generally pH 6.0 to 8.0, preferably pH 6.8 to 7.6, and more preferably pH 7.0 to 7.4.

The culture temperature is generally 30° C. to 40° C., preferably 32° C. to 37° C., and more preferably 36° C. to 37° C., and the culture temperature may be changed during the culture.

The cultivation is preferably performed in an atmosphere having a $CO_2$ concentration of 0% to 40%, and preferably 2% to 10%.

The culture time is not particularly limited, but is generally 12 hours to 90 days, preferably 24 hours to 60 days, more preferably 24 hours to 30 days.

In the culture, the medium can be replaced, aerated, and agitated depending on the necessity.

The animal cells of the present invention can be cultured in a culture device (also referred to as a bioreactor) or other suitable containers. Examples of the culture device include a fermenter tank culture device, an air lift culture device, a culture flask culture device, a spinner flask culture device, a microcarrier culture device, a fluidized bed culture device, a hollow fiber culture device, and a roller bottle culture device. A culture can be performed using a type culture device, a filling tank type culture device, or the like.

The culture scale is generally from 1 L to 20,000 L, preferably from 200 L to 2,000 L, and more preferably from 500 L to 2,000 L.

The culture may be performed using any method such as batch culture, fed-batch culture (also referred to as feeding culture), or perfusion culture, but the fed-batch culture or the perfusion culture is preferable.

The batch culture is a discontinuous method in which cells are proliferated for a short period in a fixed-volume culture medium, and then are completely harvested. A culture product proliferated using the batch method experiences an increase in cell density until reaching a maximum cell density, and then culture components are consumed and levels of metabolic by-products (lactate, ammonia, and the like) accumulate, which causes a viable cell density to decline. Harvesting typically occurs at a time when the maximum cell density (typically, 5 to $10 \times 10^6$ cells/mL) is achieved. A batch process is the simplest culture method, but the viable cell density is limited by nutrient availability, and once the cells reach the maximum density, the culture is declined and the production of the target protein is reduced. Since accumulation of waste products and nutrient depletion rapidly lead to culture decline (typically approximately 3 to 7 days), it is not possible to extend the duration of production of the target protein.

The fed-batch culture is a culture method that improves the batch process by feeding a bolus or continuous medium and replenishing the consumed medium components. That is, in the fed-batch culture, the culture form is suspension culture, which provides additional components to the culture at one or more points after the start of the culture process. Examples of the additional components include nutrition supplement components for cells that are depleted during the culture process, and may include other auxiliary components (for example, cell cycle inhibiting compounds).

In the fed-batch culture, since additional nutrients are added throughout the culture period, there is a possibility that higher cell densities and higher yields of the target protein may be achieved compared to the batch culture. In the fed-batch culture, unlike the batch culture, it is possible to prepare and maintain a two-phase culture by operating the feeding schedule and the culture components such that a period (proliferation phase) of cell proliferation for achieving a desired cell density is distinguished from a period (production period) of stopped or slow cell proliferation. In this manner, there is a possibility that the fed-batch culture can achieve a higher production amount of the target protein compared to the batch culture.

In fed-batch culture or batch culture, a seeded cell density of the cell culture is generally from $0.2 \times 10^6$ cells/mL to $1 \times 10^7$ cells/mL, preferably from $0.2 \times 10^6$ cells/mL to $5 \times 10^6$ cells/mL, more preferably $0.5 \times 10^6$ cells/mL or more to $2.5 \times 10^6$ cells/mL, and further more preferably $0.5 \times 10^6$ cells/mL to $1.5 \times 10^6$ cells/mL.

In the fed-batch culture or batch culture, the viable cell rate during the culture period is preferably 60% to 100%, more preferably 70% to 100%, and further more preferably 75% to 100% in the entire period.

In the fed-batch culture or batch culture, a maximum concentration of an isovaleric acid in the culture solution throughout the culture period is preferably 3,000 µmol/L or less, more preferably 1,500 µmol/L or less, and further more preferably 1,000 µmol/L or less, particularly preferably 500 µmol/L, and most preferably 300 µmol/L or less. A lower limit of the maximum concentration of an isovaleric acid in the culture solution throughout the culture period is not particularly limited, but is generally 1 µmol/L or more.

In the fed-batch culture or batch culture, a secretion amount of the isovaleric acid per cell throughout the culture period is preferably 30 fmol/cell/day or less, more preferably 15 fmol/cell/day or less, and further more preferably 5 fmol/cell or less. A lower limit of the secretion amount of the isovaleric acid per cell throughout the culture period is not particularly limited, but is generally 0.1 fmol/cell/day or more.

In the fed-batch culture or batch culture, a maximum concentration of a butyric acid in the culture solution throughout the culture period is preferably 3,000 µmol/L or less, more preferably 1,500 µmol/L or less, further more preferably 1,000 µmol/L or less, particularly preferably 500 µmol/L, and most preferably 300 µmol/L or less. The lower limit of the maximum concentration of the butyric acid in the culture solution throughout the culture period is not particularly limited, but is generally 1 µmol/L or more.

In the fed-batch culture or batch culture, the secretion amount of the butyric acid per cell throughout the culture period is preferably 30 fmol/cell/day or less, more preferably 15 fmol/cell/day or less, and further more preferably 5 fmol/cell/day or less. The lower limit of the secretion amount of the butyric acid per cell throughout the culture period is not particularly limited, but is generally 0.1 fmol/cell/day or more.

The perfusion culture is a culture method in which fresh medium is added and a used medium is removed at the same time, and there is a possibility that the batch culture and the fed-batch culture can be further improved. According to the perfusion culture, it is possible to achieve a high cell density exceeding $1 \times 10^8$ cells/mL. A typical perfusion culture starts with a batch culture start-up lasting one or two days, then, a fresh feed medium is continuously, in stages, and/or intermittently added to the culture product, and the used medium is removed at the same time. In the perfusion culture, it is possible to remove a used medium while maintaining a cell density using a method such as sedimentation, centrifugation, or filtration.

The advantage of the perfusion culture is that the culture in which a target protein is produced is maintained for a longer period than the batch culture method or the fed-batch culture. However, in order to maintain a long-term perfusion culture, particularly a perfusion culture at a high cell density, preparation, use, storage, and disposal of a medium are required. In the perfusion culture, many nutrients are required, and the production cost of the target protein tends to be higher than that in the batch culture and the fed-batch culture. In addition, since it is possible to continue culture while harvesting antibodies out of the system by selecting a membrane pore diameter, a retention time in a culture solution of the antibodies is shortened, it is possible to keep the quality of the antibody high by shortening a retention time and reducing chemical change.

As described above, the perfusion culture enables the high cell density culture by performing the culture by feeding the fresh medium while extracting the medium in order to suppress accumulation of waste products, but there was a problem in that high cost is caused since a large amount of the medium is used. However, according to the animal cells of the present invention, a high cell density culture is possible even at a low perfusion ratio by reducing the isovaleric acid and the butyric acid, which are substances causing proliferation inhibition, and since the production amount and the productivity of the target protein are not decreased, this can contribute to cost reduction.

It is also possible to perform a culture in which the fed-batch culture and the perfusion culture are combined to each other. As an example, it is possible to use fed-batch culture with a bolus feed to maintain the culture of cells in the proliferation period, and subsequently, it is possible to use perfusion culture to produce a target protein.

Perfusion may be in any form of continuous perfusion, stepwise perfusion, intermittent perfusion, or a combination thereof. Animal cells are retained in the culture product and the used medium that is removed may substantially do not include cells or may have much fewer cells than the culture product. The target protein expressed by a cell culture can be retained or harvested in the culture product by selecting the membrane pore diameter. To prevent the cell density during the culture from becoming excessive, a part of the culture solution may be extracted together with the cells, and the cell density may be reduced (cell bleeding) by adding the same amount of the fresh medium.

In the perfusion culture, the seeded cell density of the cell culture is generally $0.2 \times 10^6$ cells/mL to $3 \times 10^7$ cells/mL, and preferably $0.5 \times 10^6$ cells/mL to $1 \times 10^7$ cells/mL.

In the perfusion culture, the viable cell rate during the culture period is preferably 80% or more, more preferably 85% or more, and further more preferably 90% or more in the entire period.

In the perfusion culture, the highest attainable cell density is preferably $2 \times 10^8$ cells/mL or less, more preferably $1.5 \times 10^8$ cells/mL or less, and further more preferably $1.0 \times 10^8$ cells/mL or less.

In the perfusion culture, a maximum concentration of the isovaleric acid in the culture solution throughout the culture period is preferably 3,000 µmol/L or less, more preferably 1,500 µmol/L or less, and further more preferably 1,000 µmol/L or less, particularly preferably 500 µmol/L, and most preferably at most 300 µmol/L. A lower limit of the maximum concentration of an isovaleric acid in the culture solution throughout the culture period is not particularly limited, but is generally 1 µmol/L or more.

In the perfusion culture, the secretion amount of the isovaleric acid per cell throughout the culture period is preferably 30 fmol/cell/day or less, more preferably 15 fmol/cell/day or less, and further more preferably 5 fmol/cell/day or less. A lower limit of the secretion amount of the isovaleric acid per cell throughout the culture period is not particularly limited, but is generally 0.1 fmol/cell/day or more.

In the perfusion culture, a maximum concentration of the butyric acid in the culture solution throughout the culture period is preferably 3,000 µmol/L or less, more preferably 1,500 µmol/L or less, further more preferably 1,000 µmol/L or less, particularly preferably 500 µmol/L or less, and most preferably 300 µmol/L or less. The lower limit of the maximum concentration of the butyric acid in the culture solution throughout the culture period is not particularly limited, but is generally 1 µmol/L or more.

In the perfusion culture, the secretion amount of the butyric acid per cell throughout the culture period is preferably 30 fmol/cell/day or less, more preferably 15 fmol/cell/day or less, and further more preferably 5 fmol/cell/day or less. The lower limit of the secretion amount of the butyric acid per cell throughout the culture period is not particularly limited, but is generally 0.1 fmol/cell/day or more.

The perfusion ratio in the perfusion culture is preferably 0.3 vvd to 5.0 vvd, and more preferably from 0.3 vvd to 1.5 vvd. Here, vvd represents the following.

vvd=(volume of fresh medium/working volume of reactor/day, amount of culture solution per day/feed amount of culture solution)

The seeded cell density in the cell culture and the highest attainable cell density in the culture can be determined by measuring the number of cells by a conventional method and dividing the number of cells by the amount of the culture solution.

The viable cell rate (survival rate) during the culture period is determined by dividing the number of viable cells by (the number of viable cells+ the number of dead cells). For example, the number of cells can be measured using Vi-CELL XR (Beckman Coulter Corporation). The concentration of the isovaleric acid in the culture solution can be measured by chromatographic separation (for example, chromatographic separation using ICS-2100 and Ion Pac AS11-HC column manufactured by DIONEX Corporation).

The secretion amount of the isovaleric acid and the secretion amount of the butyric acid per cell can be obtained from the mathematical formulas described in Examples described later.

The target protein produced by the above-described culture can be purified. The separation and purification of the target protein may be performed by the separation and purification methods used for normal proteins. For example, it is possible to perform separation and purification of the target protein by appropriately selecting and combining a chromatography column such as affinity chromatography, a filter, ultrafiltration, salting out, dialysis, sodium dodecyl sulfate (SDS) polyacrylamide gel electrophoresis, isoelectric focusing, and the like, but is not limited thereto. The concentration of the target protein obtained as described above can be measured by absorbance measurement or enzyme-linked immunosorbent assay (ELISA).

Columns used for affinity chromatography include a protein A column and a protein G column. Examples of the chromatography other than affinity chromatography include ion exchange chromatography, hydrophobic chromatography, gel filtration, reverse phase chromatography, and adsorption chromatography. The chromatography thereof can be performed using liquid phase chromatography such as high-performance liquid chromatography (HPLC) or fast protein liquid chromatography (FPLC).

In addition, it is possible to modify the target protein by causing appropriate polypeptide modifying enzyme to act on before or after purification, or it is possible to partially remove the peptide. As the polypeptide modifying enzyme, for example, trypsin, chymotrypsin, lysyl endopeptidase, protein kinase, glucosidase, and the like are used.

[Use of Target Protein]

In a case where the target protein produced by the method of the present invention has useful biological activity as a pharmaceutical, it is possible to produce pharmaceuticals by mixing the target protein with a pharmaceutically acceptable carrier or additive and formulating thereof.

Examples of pharmaceutically acceptable carriers and additives include water, pharmaceutically acceptable organic solvents, collagen, polyvinyl alcohol, polyvinyl pyrrolidone, carboxy vinyl polymer, sodium carboxymethylcellulose, sodium polyacrylate, sodium alginate, aqueous Dextran, sodium carboxymethyl starch, pectin, methylcellulose, ethylcellulose, xanthan gum, gum arabic, casein, agar, polyethylene glycol, diglycerin, glycerin, propylene glycol, petrolatum, paraffin, stearyl alcohol, stearic acid, human serum albumin (HSA) Mannitol, sorbitol, lactose, pharmaceutically acceptable surfactants, and the like.

For example, in a case of being used as an injectable preparation, it is possible to dissolve the purified target protein in a solvent such as physiological saline, a buffer solution, a glucose solution, or the like, and to use those obtained by adding an anti-adsorption agent such as Tween 80, Tween 20, gelatin, human serum albumin, or the like thereto. Alternatively, a freeze-dried product may be used for dissolving and reconstituting the product before use, and sugar alcohol or sugar such as mannitol or glucose can be used as the excipient for freeze-drying, for example.

A method of administering the target protein may be either of oral administration or parenteral administration, but is preferably parenteral administration. Examples thereof include injection (for example, systemic or local administration by intravenous injection, intramuscular injection, intraperitoneal injection, subcutaneous injection, and the like), nasal administration, pulmonary administration, transdermal administration, and the like.

The dose of the target protein is appropriately selected depending on the kind of the target protein, the kind of the disease to be treated or prevented, the age of the patient, the severity of the disease, and the like. Generally, the dose is in a range of 0.001 mg to 1,000 mg per kg of body weight at a time, but is not particularly limited thereto.

The present invention will be described more specifically with reference to the following examples, but the present invention is not limited to the examples.

EXAMPLES

<Example 1> Preparation of Animal Cell

A vector containing a nucleic acid sequence encoding chimeric IgG1 (rituximab) was constructed, and the constructed vector was introduced into CHO-DG44 cells, whereby CHO-DG44 cells expressing IgG1 (IgG1 cells) were produced. Construction of the vector and introduction thereof into the cell were performed according to Example 2 of JP2016-517691A.

Figure 2:
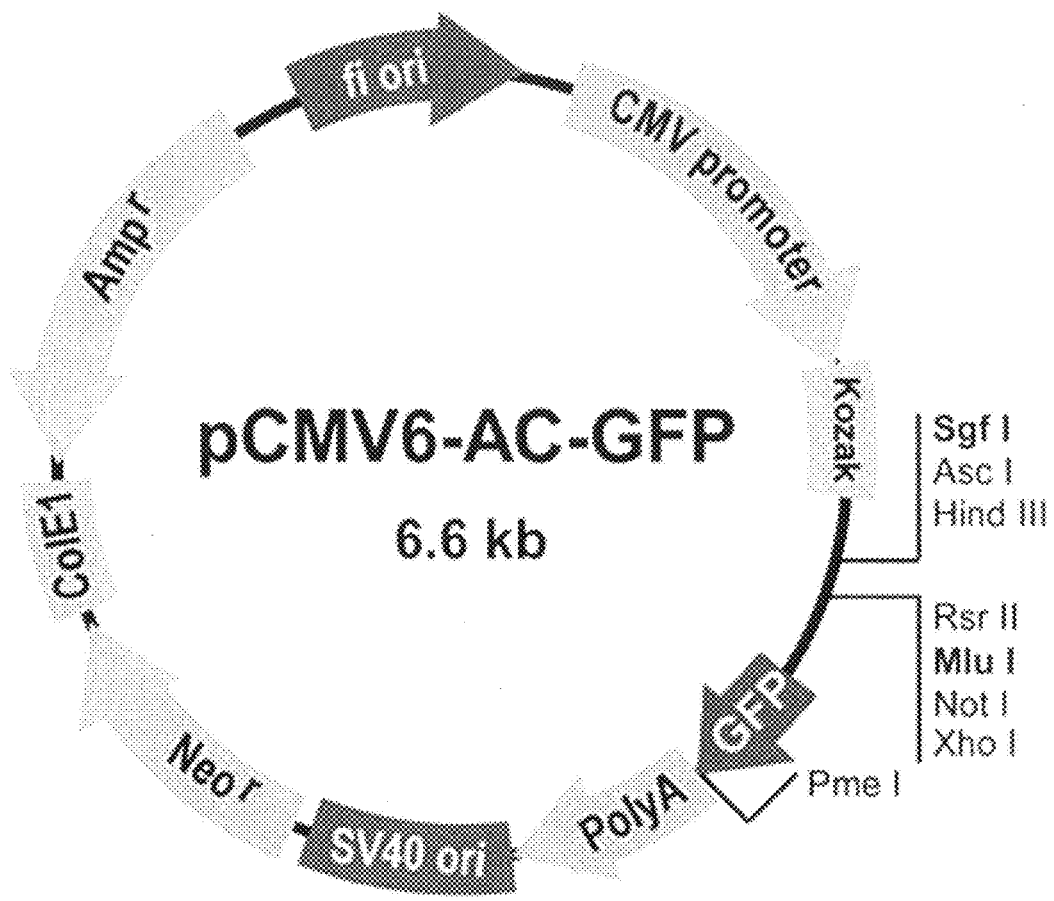
FIG. 2 illustrates a schematic diagram of a vector (pCMV6-AC-GFP) containing a gene hIVD-GFP encoding a human isovaleryl-CoA dehydrogenase conjugated to a green fluorescent protein (GFP). In the pCMV6-AC-GFP, a gene hIVD encoding a human isovaleryl-CoA dehydrogenase is incorporated into a restriction enzyme site upstream of the GFP.

A vector (pCMV6-AC-GFP: FIG. 2) containing the gene IVD-GFP encoding a human isovaleryl-CoA dehydrogenase conjugated with green fluorescent protein (GFP) was purchased (OriGene Corporation).

Figure 3:
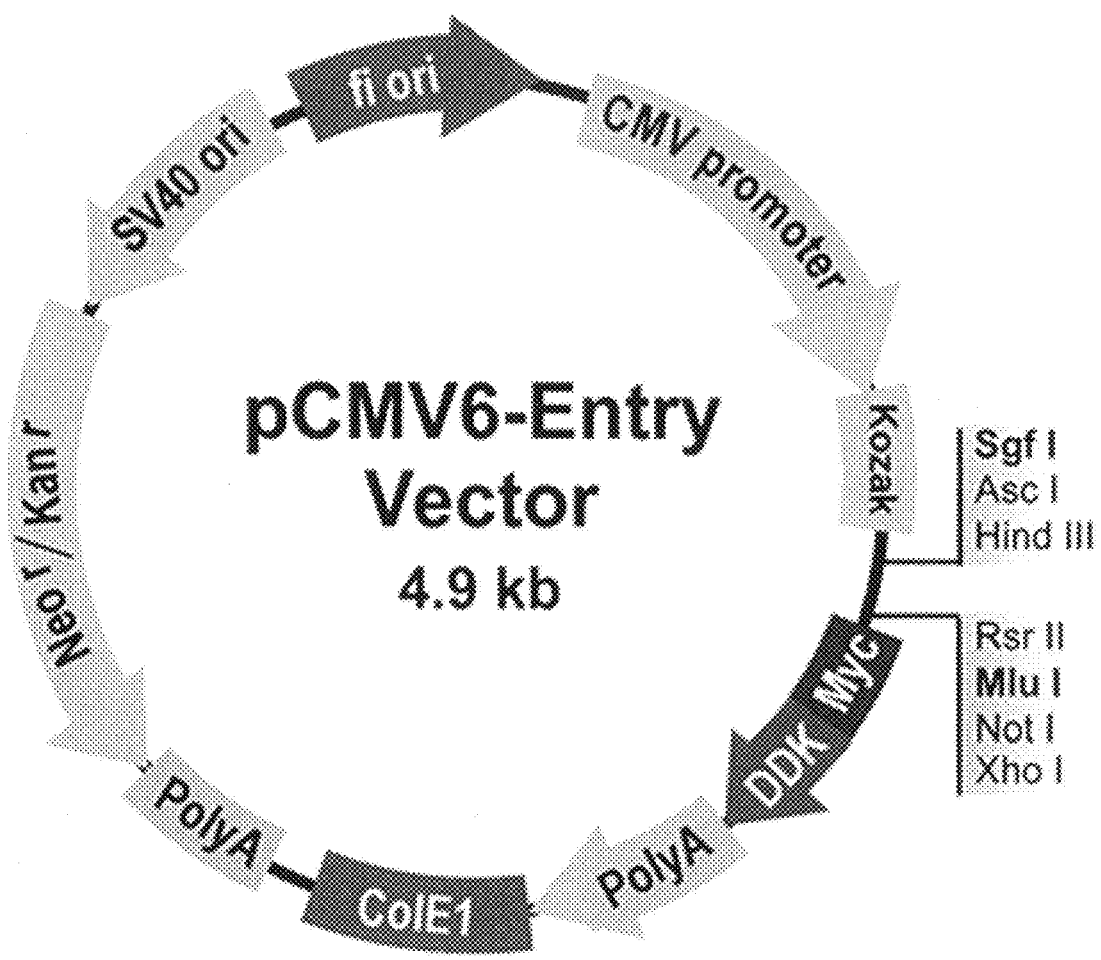
FIG. 3 illustrates a schematic diagram of a pCMV6-Entry vector.

In addition, a pCMV6-Entry Vector (FIG. 3) (OriGene Corporation) was purchased and used as a control group not expressing IVD-GFP.

CHO-DG44 cells expressing IgG1 (IgG1 cells) were all cultured in an incubator at 37° C. in a 5% $CO_2$ atmosphere. The above vector was introduced into $1 \times 10^6$ cells of IgG1 cells by electroporation (Lonza Corporation, 4D-Nucleofector), and the cells were seeded in 2 mL of OptiCHO (Life Technologies Corporation, 12681011) medium. After one day, G418 (Life Technologies Corporation) was added so as to be a final concentration of 200 μg/mL. On the 7th day after gene introduction, the cells were seeded in 200 μL of medium at 5,000 cells/well per 96-well plate (IWAKI, 3860-096), and G418 (Life Technologies Corporation) was added to a final concentration of 20 μg/mL.

Figure 4:
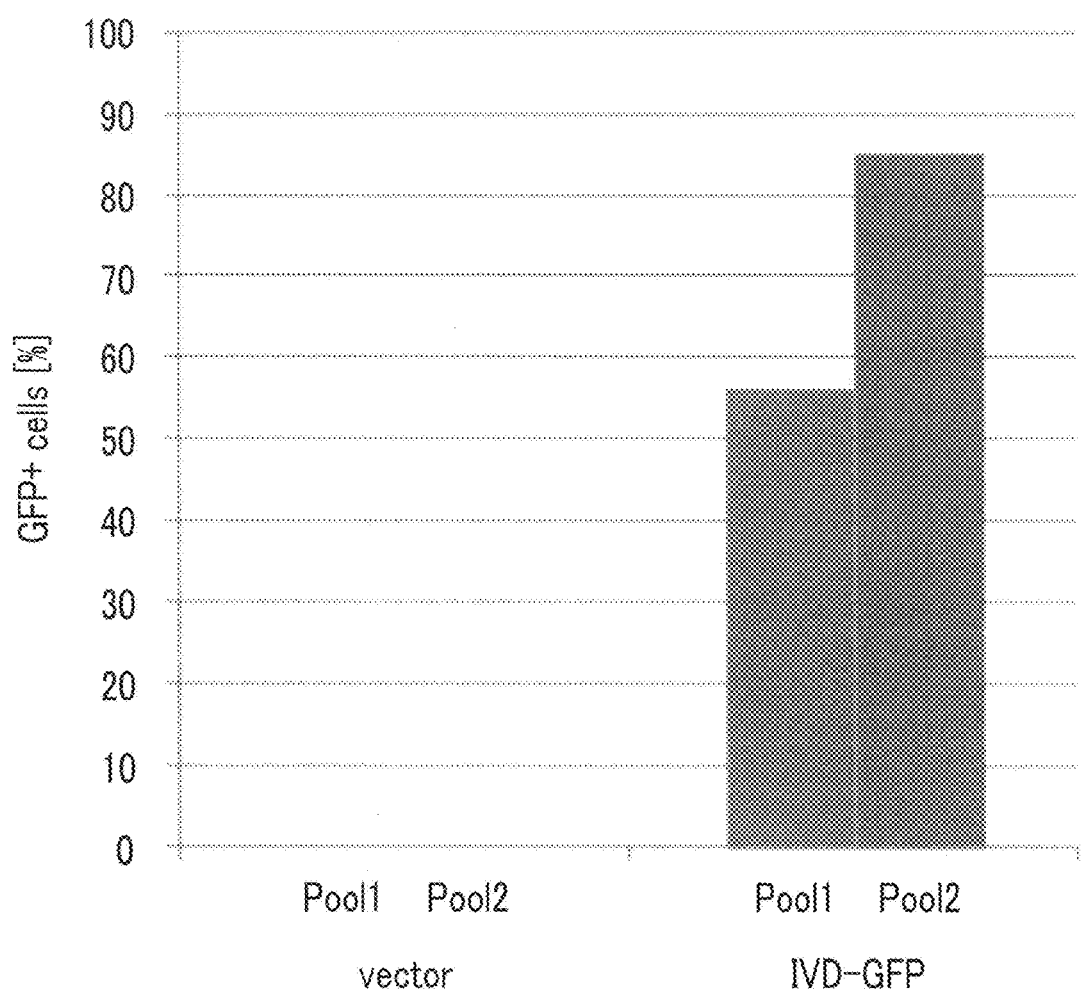
FIG. 4 illustrates a result of measuring the fluorescence of cells after gene introduction and measuring a proportion of cells that emit a fluorescent signal.

On the 18th day after gene introduction, the culture solution amount was expanded to 1 mL and transferred to a 24-well plate. The fluorescence of the IVD-GFP-expressing cells was measured using a flow cytometer (BD FACSCalibur, BD Biosciences Corporation), and cells emitting a fluorescent signal were selected. FIG. 4 illustrates a result of measuring the ratio of cells (GFP+ cells) that emit a fluorescent signal.

Figure 5:
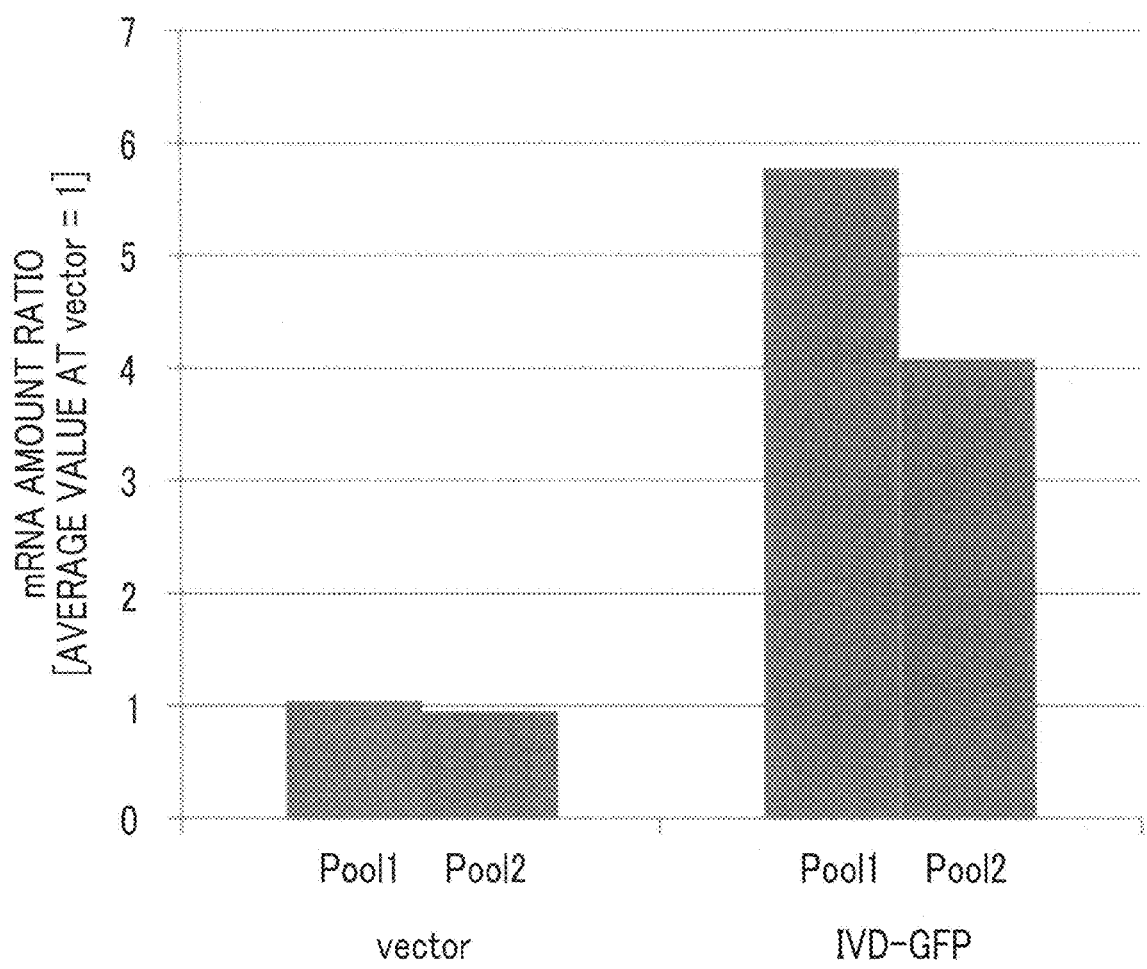
FIG. 5 illustrates a result of confirming expression of an IVD gene in cells after gene introduction.

In addition, cells were treated with RNeasy plus mini kit (Qiagen) to harvest Total RNA. Reverse transcription was performed on the obtained Total RNA using PrimeScript™ RT Master Mix (Perfect Real Time, Takara). Primers homologous to both of endogenous and exogenous IVD (SEQ ID NOs: 3 and 4) and primers to the β-actin gene (SEQ ID NOs: 5 and 6) as an internal standard were designed and real-time PCR (polymerase chain reaction) using SYBR (registered trademark) Premix Ex Taq™ (Tli RNaseH Plus, Takara) was performed. The result of confirming expression of the IVD gene by using β-actin for standardization is shown in FIG. 5. In the cells into which the IVD gene was introduced, the expression of IVD was increased by about 4 to 6 times (FIG. 5).

In FIGS. 4 and 5, the Vector indicates a cell into which the pCMV6-Entry Vector has been introduced, and the IVD-GFP indicates a cell into which a vector containing IVD-GFP has been introduced. Pool1 and Pool2 indicate the first and second tests.

Specific primers for Chinese hamster and human IVD:

```
                                          (SEQ ID NO: 3)
    Forward primer:    AGTTGATGCAGGGGAAGATG (SEQ ID NO: 4)
    Reverse primer:    TCATACAGCTTGGCATCTCG
```

Specific primers for Chinese hamster β-actin:

```
                                          (SEQ ID NO: 5)
    Forward primer:    AGCTGAGAGGGAAATTGTGCG (SEQ ID NO: 6)
    Reverse primer:    GCAACGGAACCGCTCATT
```

From the results shown in FIGS. 4 and 5, the expression of IVD in IgG1-hIVD-GFP (CHO-DG44) cells was confirmed. In both of Pool1 and Pool2, the ratio of cells expressing IVD-GFP was 50% or more. While Pool2 had a higher abundance ratio, the expression level by qPCR was lower. In comparison at GFP expressing cells× expression level, both cells are in the similar level, and the effect of reducing the isovaleric acid is similar.

On the 22nd day after the gene introduction, the culture volume was expanded to 5 mL, and a shaking culture was performed at 180 rpm and 37° C. using Tube spin (Sigma Corporation).

On the 26th day after the gene introduction, the culture volume was expanded to 20 mL, seeded in a 125 mL shaking flask (Corning), and shaking cultured at 140 rpm.

IgG1-hIVD-GFP (CHO-DG44) cells forcibly expressing a human isovaleryl-CoA dehydrogenase were established by the above-described method. In addition, gene introduction was performed on the pCMV6-Entry Vector as a control group not expressing IVD-GFP, and IgG1-vector (CHO-DG44) cells were constructed. Each gene-introduced cell was established as two kinds of pool cells.

<Example 2> Fed-Batch Culture

Fed-batch culture tests were performed on IgG1-vector (CHO-DG44) cells and IgG1-hIVD-GFP (CHO-DG44) cells, respectively, by two levels. The measurement method is as follows.

Cell number measurement method: Vi-CELL (Beckman Coulter)

Isovaleric acid measurement method: Chromatographic separation using ICS-2100 and Ion Pac AS11-HC column manufactured by DIONEX Antibody concentration measurement method: Chromatographic separation using Prominence (Shimadzu) HPLC and POROS 50A 4.6×50 mm (applied biosystems)

Figure 6:
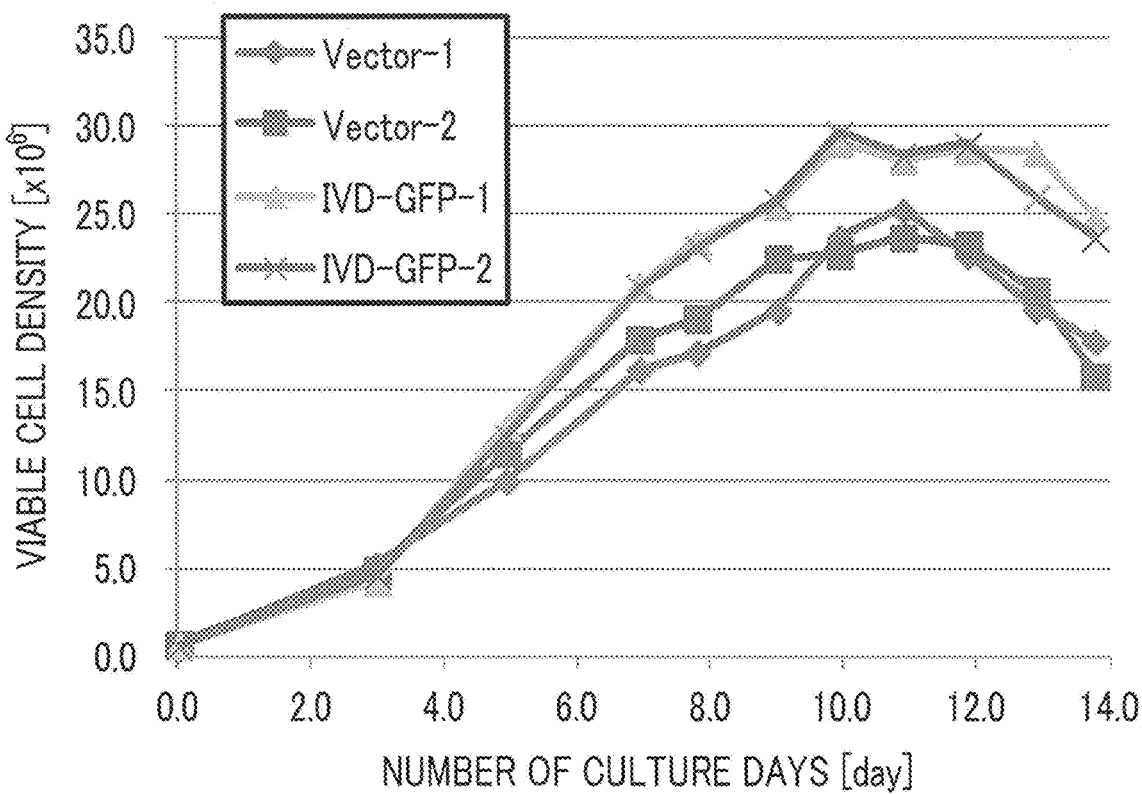
FIG. 6 illustrates a result of measuring a viable cell density of cells after gene introduction over time.
Figure 7:
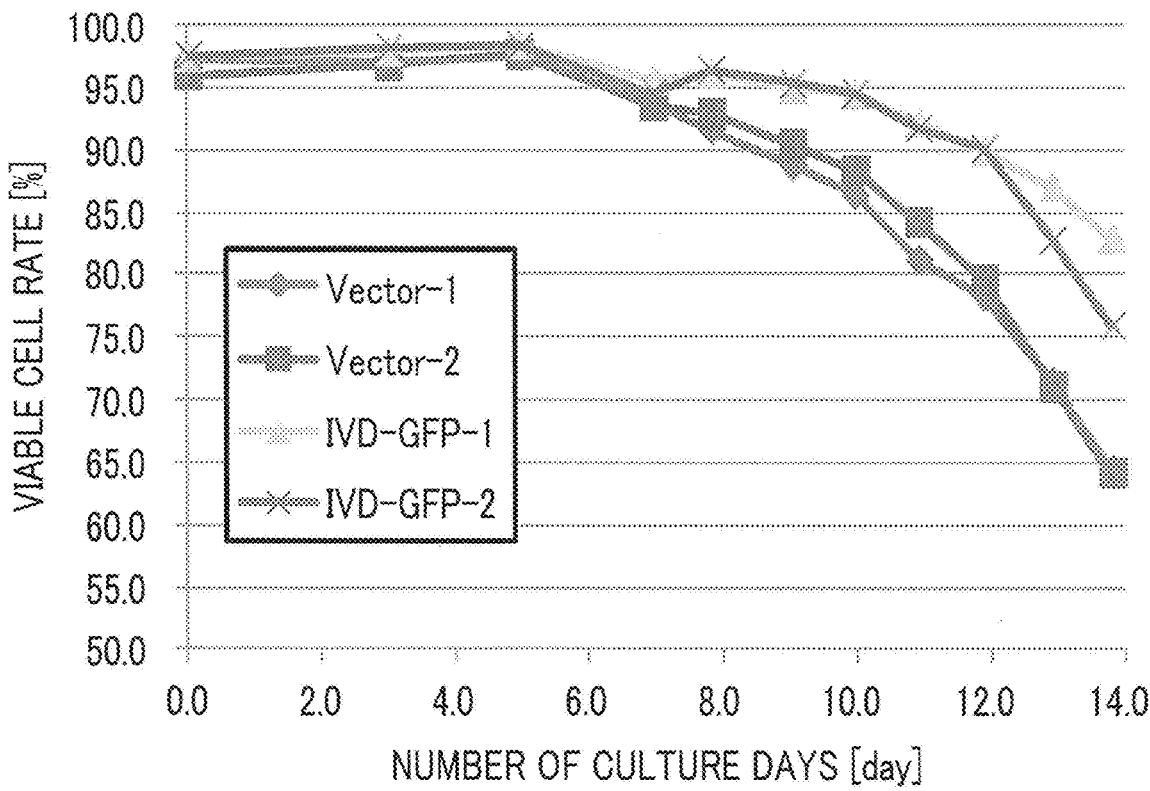
FIG. 7 illustrates a result of measuring a viable cell rate (survival rate) of cells after gene introduction over time.
Figure 8:
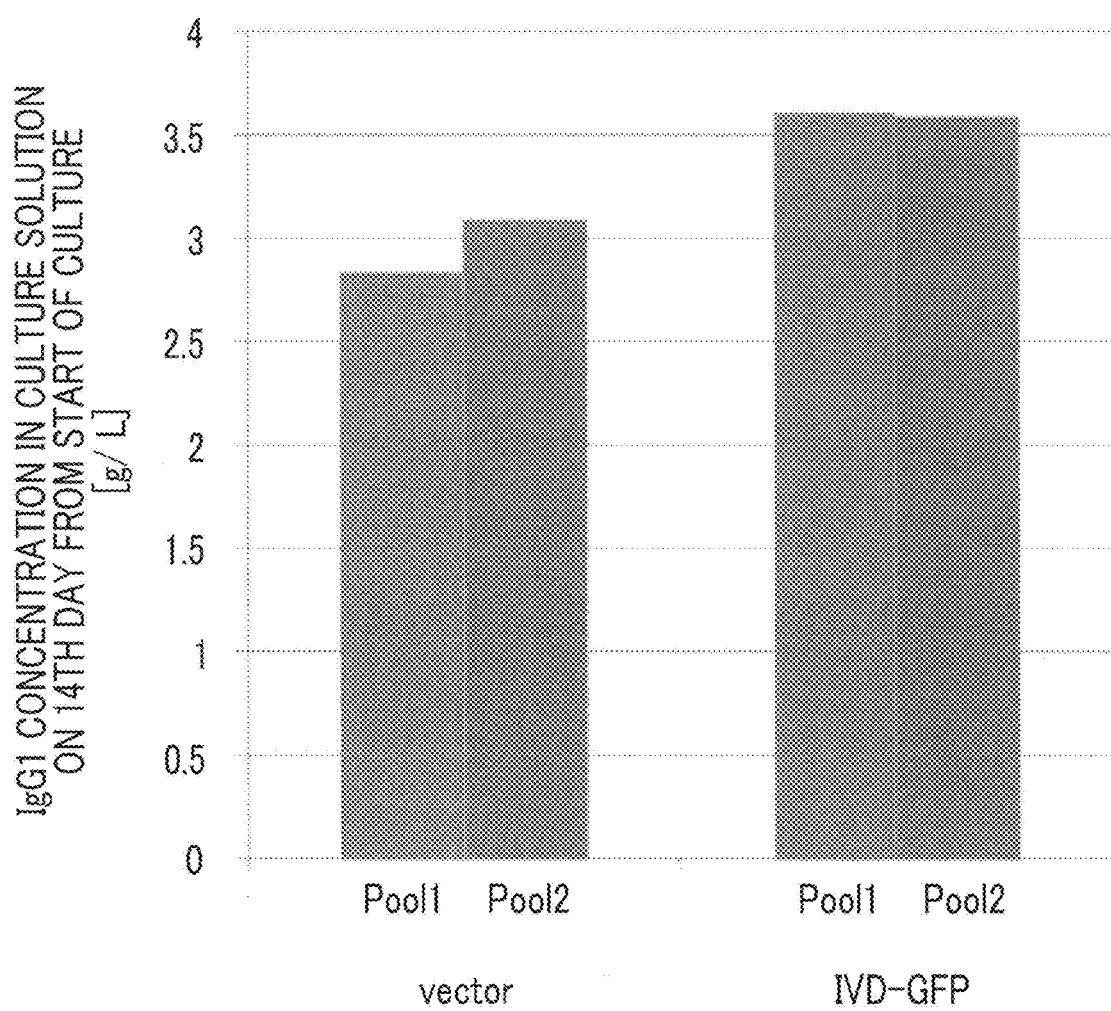
FIG. 8 illustrates a result of measuring a concentration of IgG1 in a culture solution on the 14th day after the start of culture.

The cells were suspended in a 40 mL of OptiCHO medium at a cell density of 5×10$^5$ cells/mL, seeded in a 125 mL flask, and shaking cultured at 37° C. and at a rate of 140 rpm in a 5% CO$_2$ atmosphere. From the third day to the 13th day from the start of culture, a feed medium (Cellboost 7a, 7b, GE healthcare Corporation) was added every 2% at an initial culture volume ratio every day. Sampling was performed every one to three days to measure the cell density, culture solution components, and an antibody concentration over time. For IgG1-vector (CHO-DG44) cells and IgG1-hIVD-GFP (CHO-DG44) cells, peak cell densities were observed on the 10th and 11th days from the start of culture, respectively, and IgG1-hIVD-GFP (CHO-DG44) cells could be cultured at a 20% higher cell density (FIG. 6). In addition, the cell survival rate of both cells tended to gradually decrease, but the IgG1-hIVD-GFP (CHO-DG44) cells showed an average of 15% higher survival rate on the 14th day from the start of culture (FIG. 7). On the 14th day from the start of the culture, the culture solution was harvested, and cells and cell debris were removed using a 0.22 μm-depth filter (Merck Millipore Corporation). The antibody concentration in the supernatant and the production amount of IgG per cell (Qp) were measured by liquid chromatography, and the production amount of IgG was increased by 20% on average (FIG. 8). In general, it is known that Qp decreases in a case where the proliferative properties are improved, but a decrease in Qp was not shown in IgG1-hIVD-GFP (CHO-DG44) cells (FIG. 9).

Figure 10:
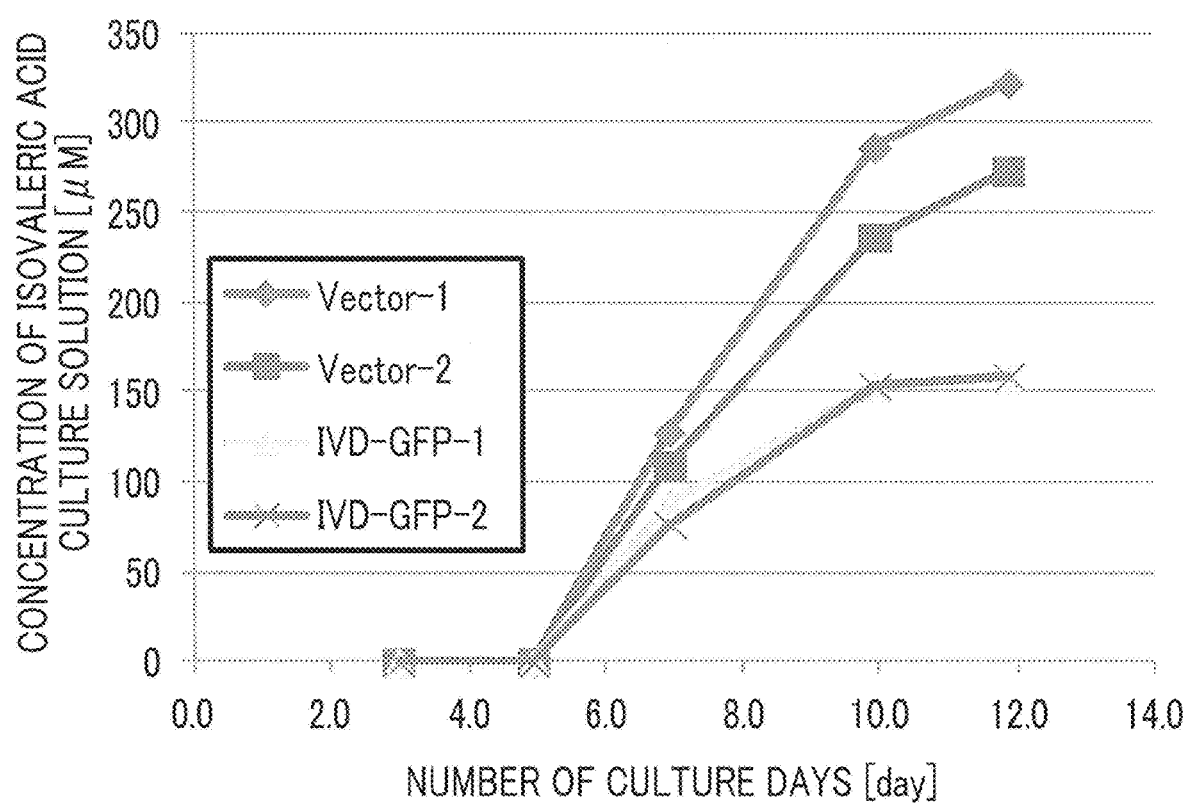
FIG. 10 illustrates a result of measuring a concentration of an isovaleric acid in a culture solution over time.

The concentration of the isovaleric acid in the culture supernatant on the 12th day from the start of the culture was measured by liquid chromatography, and IgG1-hIVD-GFP (CHO-DG44) cells showed a value lower by 46.9% (FIG. 10). The isovaleric acid is secreted in a large amount during the logarithmic proliferation phase, but the production amount of the isovaleric acid per cell ($Q_{IVA}$) was calculated from the amount of the isovaleric acid up to the 10th day from the start of the culture, and it was found that it was possible to reduce the isovaleric acid by 49% (FIG. 11).

In FIGS. 6, 7, and 10, Vector-1 and Vector-2 indicate cells into which pCMV6-Entry Vector has been introduced, and IVD-GFP-1 and IVD-GFP-2 indicate cells into which a vector containing IVD-GFP has been introduced. "-1" and "-2" indicate cells of different pools, respectively.

Figure 9:
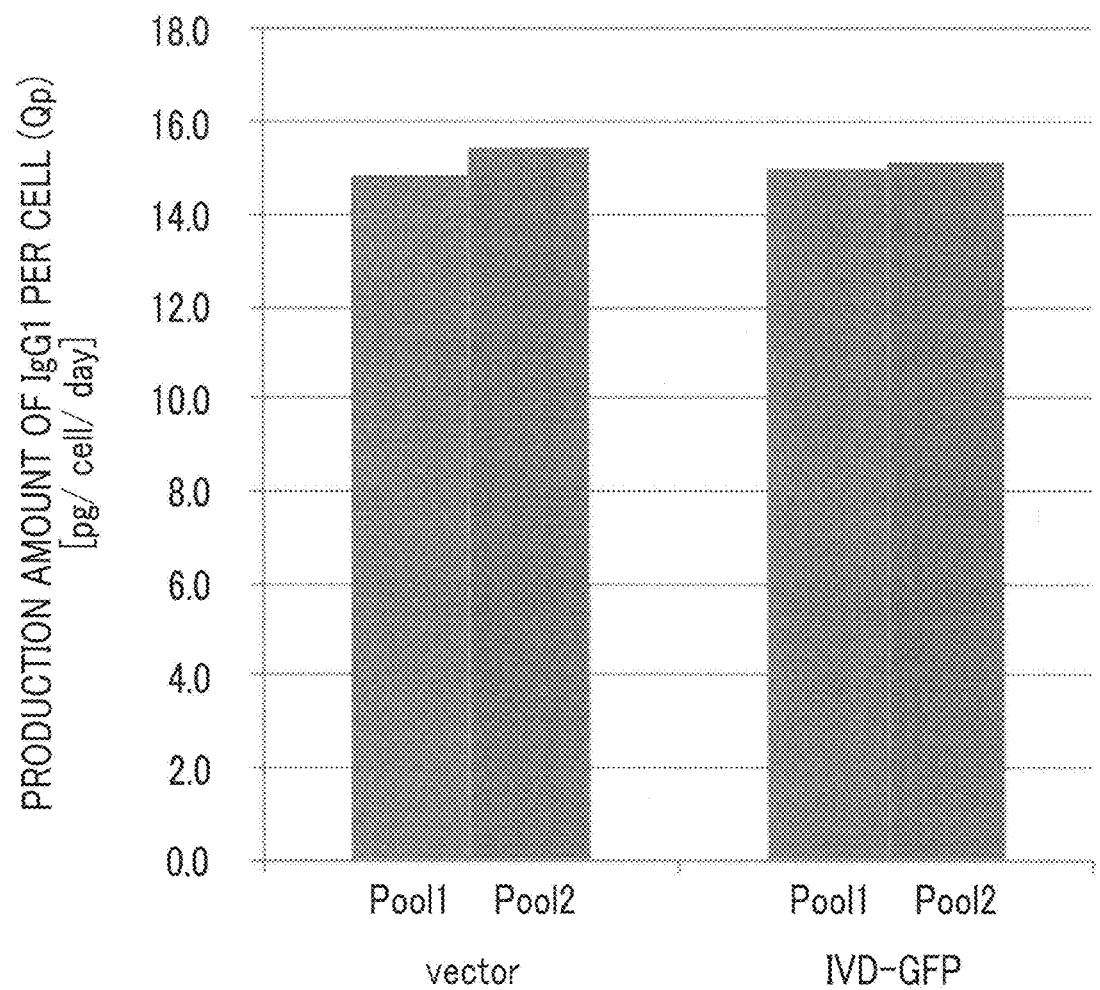
FIG. 9 illustrates a production amount of IgG1 (Qp) per cell in a culture solution on the 14th day after the start of culture.
Figure 11:
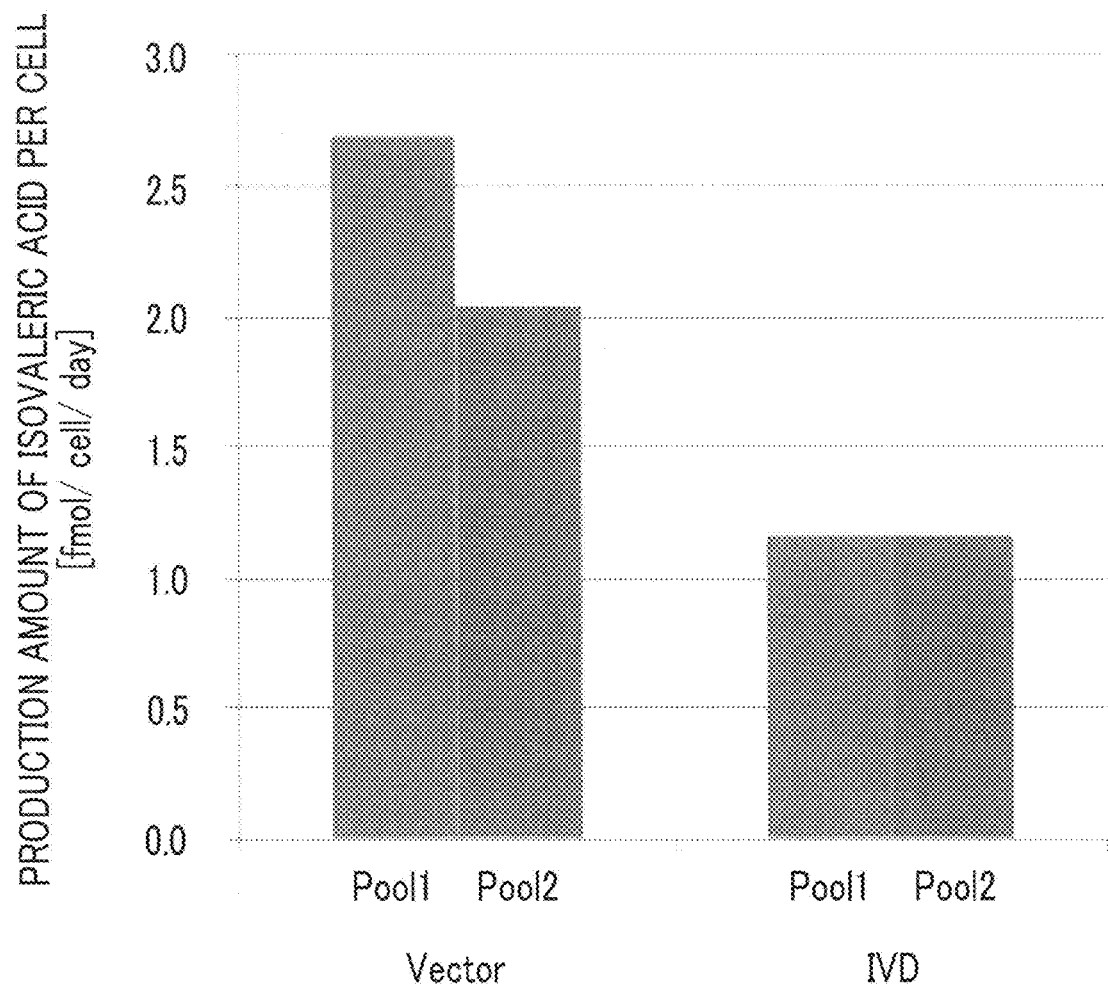
FIG. 11 illustrates a result of measuring a production amount of the isovaleric acid per cell in a culture solution.

In FIGS. 8, 9, and 11, Vectors indicate cells into which pCMV6-Entry Vector has been introduced, and IVD-GFP and IVD indicate cells into which a vector containing IVD-GFP has been introduced. Pool1 and Pool2 indicate different pools of cells, respectively.

In Examples, an antibody production amount per cell Qp [pg/cell/day], an isovaleric acid production amount per cell $Q_{IVA}$ [fmol/cell/day], and the butyric acid productivity per cell $Q_{BA}$ [fmol/cell/day] was obtained by the following formula.

$$Q_P = \frac{P_{t2} - P_{t1}}{\int_{t1}^{t2} X dt}$$ [Expression 1]

$$Q_{IVA} = \frac{A_{t2} - A_{t1}}{\int_{t1}^{t2} X dt}$$

$$Q_{BA} = \frac{B_{t2} - B_{t1}}{\int_{t1}^{t2} X dt}$$

Pti [g/L]=concentration of purified product on culture day ti

Ati [μmol/L]=concentration of isovaleric acid on culture day ti

Bti [μmol/L]=concentration of butyric acid on culture day ti

Xti [cell/day]=viable cell density on culture day ti

An approximate value of integration was calculated by obtaining the area under the proliferation curve from time t1 to t2 as the area of a trapezoid.

$$\int_{t1}^{t2} X dt \cong \sum \frac{(t_2 - t_1)(X_{t2} + X_{t1})}{2}$$ [Expression 2]

It is considered that since it is possible to improve the cell concentration and the cell survival rate without reducing Qp by decreasing the isovaleric acid, it is possible to improve the production amount of IgG. It is an unexpected effect that the proliferation ability was improved without lowering the Qp per cell.

<Example 3> Preparation of Animal Cell

A vector containing a nucleic acid sequence encoding Mab2 (anti-MUC-1 antibody) was constructed (pmab2), and a vector in which a nucleic acid sequence encoding the IVD gene was further added (pmab2/IVD) was constructed on the pmab2. By introducing the constructed vector into CHO-DG44 cells, CHO-DG44 cells expressing mab2 (mab2 cells) and CHO-DG44 cells co-expressing mab2 and IVD (mab2/IVD cells) were prepared. Construction of the vector and introduction thereof into the cell were performed according to Example 2 of JP2016-517691A.

All mab2 cells and mab2/IVD cells were cultured in an incubator at 37° C. in a 5% CO$_2$ atmosphere. The vector was introduced into mab2 cells and mab2/IVD cells 5×10$^6$ cells using an electroporation method (Lonza Corporation, 4D-Nucleofector), and was seeded in a 100 times-diluted 20 mL of OptiCHO (Life Technologies Corporation, 12681011) medium containing HT Supplement (100×) (Life Technologies Corporation, 11067-030). Transfection was independently performed eight times, and one day later, the medium was replaced with an Opti-CHO medium to remove HT Supplement, and methotrexate (Wako Pure Chemical Industries, 139-13571) was added so as to be at a final concentration of 175 nmol/L. On the 14th day after the gene introduction, the culture volume was expanded to 20 mL, seeded in a 125 mL shaking flask (Corning), and shaking cultured at 140 rpm.

Figure 12:
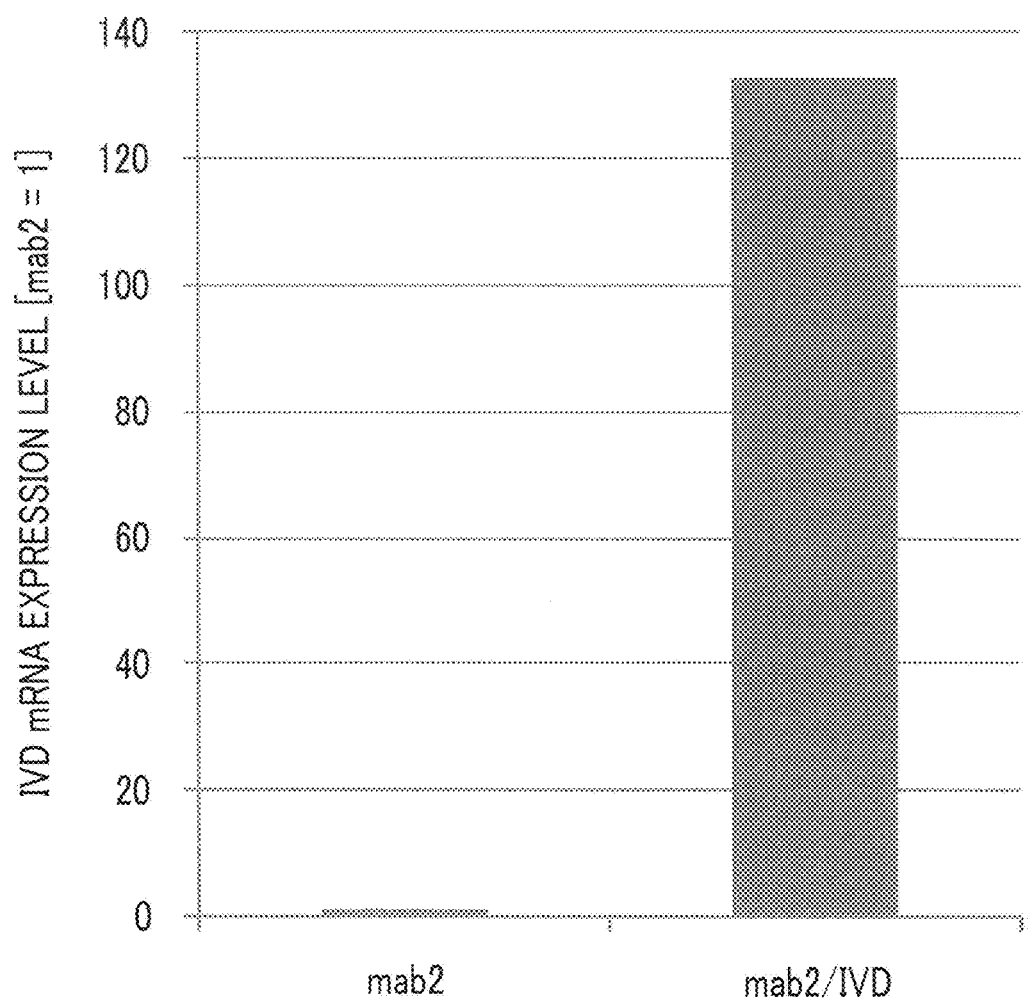
FIG. 12 illustrates a result of measuring expression of the IVD gene.

In addition, cells were treated with RNeasy plus mini kit (Qiagen) to harvest Total RNA. Reverse transcription was performed on the obtained Total RNA using PrimeScript™ RT Master Mix (Perfect Real Time, Takara). Primers homologous to both endogenous and exogenous IVD (SEQ ID NOS: 3 and 4) and primers to the Hprt1 gene (SEQ ID NOs: 7 and 8) as an internal standard were designed and real-time PCR (polymerase chain reaction) using SYBR (registered trademark) Premix Ex Taq™ (Tli RNaseH Plus, Takara) was performed. The result of confirming expression of the IVD gene using Hprt1 for standardization is shown in FIG. 12. In the cells into which the IVD gene was introduced, the expression of IVD was increased about 136 times on average (FIG. 12). Compared with Example 1, it was possible to obtain cells with higher gene expression of IVD than those in which IVD gene was introduced into the same vector as the target protein.

Specific primers for Chinese hamster Hprt1:

```
                                         (SEQ ID NO: 7)
Forward primer:    TCGAGGATTTGGAAAAGGTG (SEQ ID NO: 8)
Reverse primer:    AATCCAGCAGGTCAGCAAAG
```

<Example 4> Batch Culture Test

A batch culture test was performed using mab2 cells (8 kinds) and mab2/IVD cells (8 kinds), respectively. The cells were suspended at a cell density of $4 \times 10^5$ cells/mL in 30 mL of a 20 mL OptiCHO (Life Technologies Corporation, 12681011) containing HT Supplement (100×) (Life Technologies Corporation, 11067-030), seeded in a 125 mL flask, and shaking cultured at 37° C. and at a rate of 140 rpm in a 5% $CO_2$ atmosphere. Sampling was performed on 0, 2, 3, 6, and 7 days from the start of the culture in order to measure the cell density, the culture solution component, and the antibody concentration over time.

Figure 13:
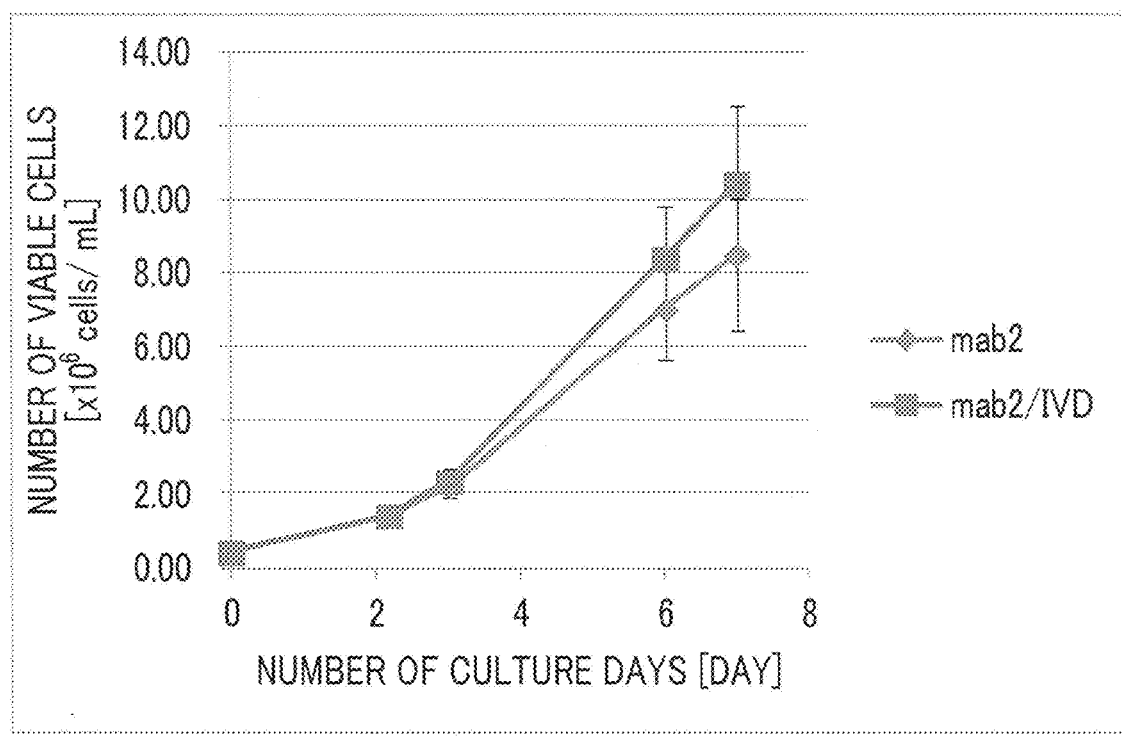
FIG. 13 illustrates a result of measuring the viable cell density of cells over time.
Figure 14:
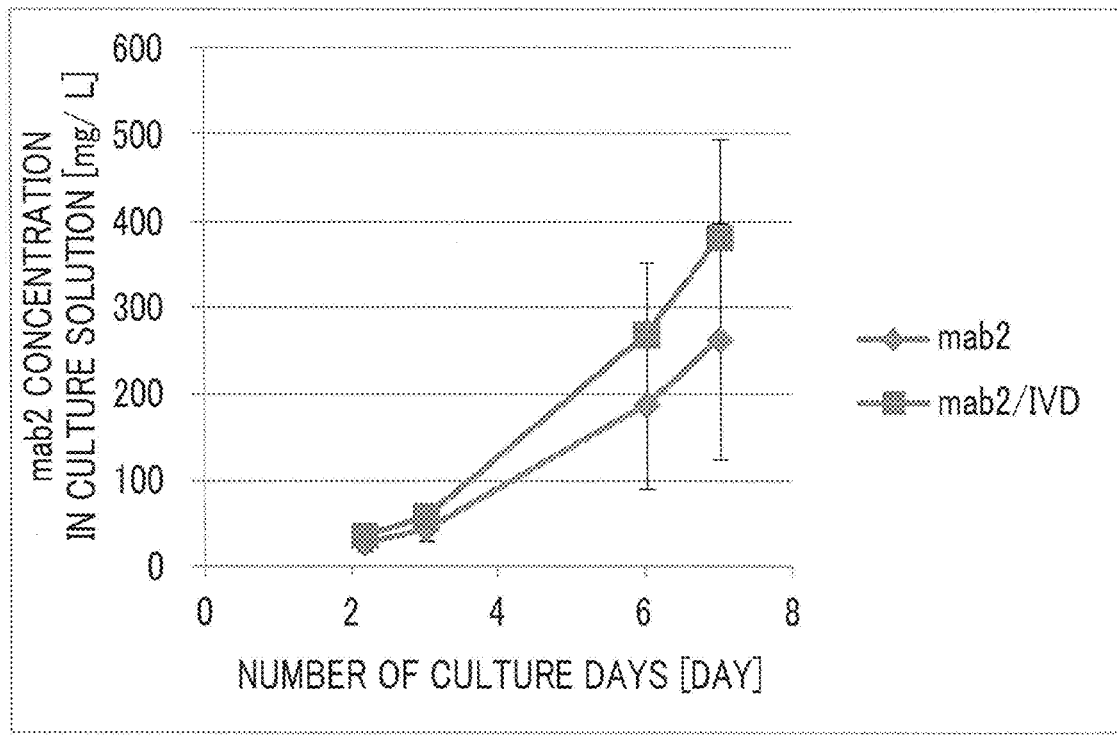
FIG. 14 illustrates a result of measuring a concentration of monoclonal antibodies in a culture solution over time.
Figure 15:
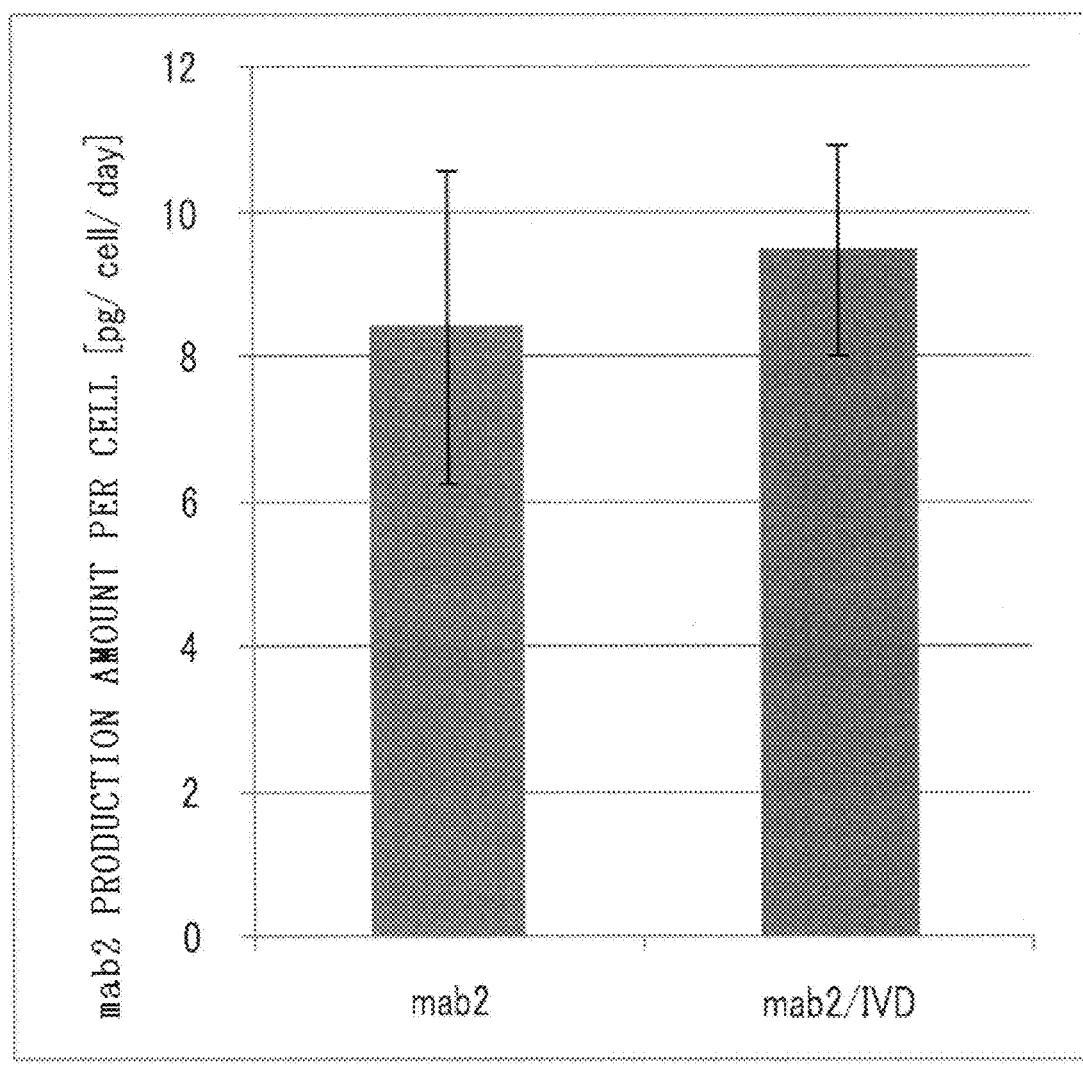
FIG. 15 illustrates a production amount of the monoclonal antibodies per cell.

The mab2 (CHO-DG44) cells and the mab2/IVD (CHO-DG44) cells were each cultured for 7 days, and the mab2/IVD (CHO-DG44) cells could be cultured at a cell density of 19% higher on the 7th day from the start of the culture. (FIG. 13). The concentration of mab2 in the supernatant was measured by Cede x Bio (Roche Diagnostics), and the production amount of mab2 was increased by 31% on average on the 7th day from the start of the culture (FIG. 14). In general, it is known that Qp decreases in a case where proliferative properties are improved, but in the mab2/IVD (CHO-DG44) cells, reduction of Qp was not found, and conversely, there was a result that Qp was improved by 11% on average (FIG. 15).

Figure 16:
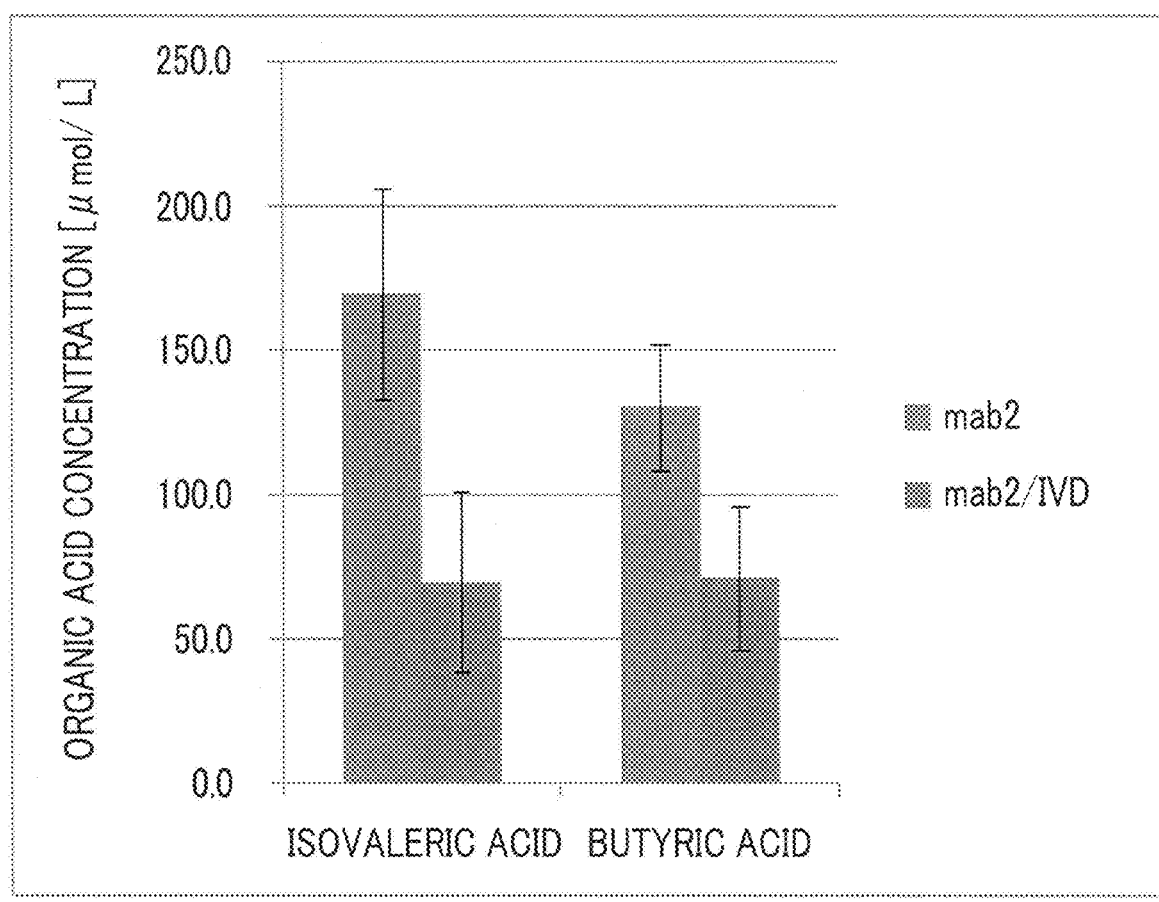
FIG. 16 illustrates a result of measuring a concentration of an organic acid in a culture solution.
Figure 17:
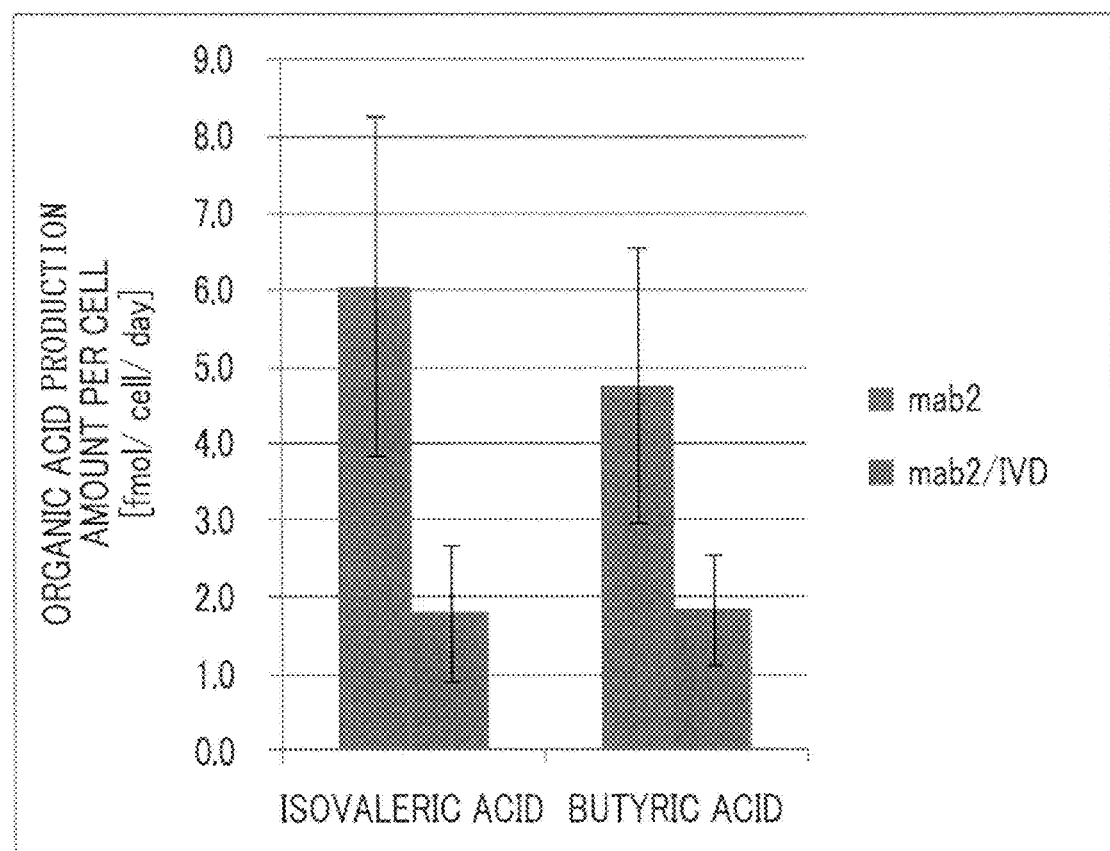
FIG. 17 illustrates an amount of organic acids per cell in a culture solution.

The concentrations of the isovaleric acid and the butyric acid in the culture supernatant on the 7th day from the start of the culture were measured by liquid chromatography, and the mab2/IVD (CHO-DG44) cells showed values lower by 59% and 45%, respectively (FIG. 16). The isovaleric acid and the butyric acid are secreted in a large amount during the logarithmic proliferation phase, but the production amount of the isovaleric acid per cell ($Q_{IVA}$) and the generation amount of the butyric acid ($Q_{BA}$) were calculated from the amount of isovaleric acid up to 10 days from the start of the culture, and it was found that it is possible to reduce thereof by 70% and 61%, respectively (FIG. 17).

It is known that butyric acid has proliferation inhibitory activity similar to the isovaleric acid, but it is an unexpected result that IVD was able to reduce the secretion amount even though it is not directly involved in the metabolic pathway of butyric acid generation.

<Example 5> Perfusion Culture Test

Perfusion culture tests were performed using mab2 (CHO-DG44) cells and mab2-IVD (CHO-DG44) cells.

The cells were seeded in a bioreactor at a cell density of $25 \times 10^5$ cells/mL, and stirred and cultured at 37° C. and at a rate of 200 rpm in a 5% $CO_2$ atmosphere. The perfusion ratio was gradually increased from 0.3 vvd to 1.2 vvd by perfusion using a hollow fiber membrane and an ATF pump for separation to keep the cells in the culture tank, and the perfusion ratio was reduced in phases and cultured at some level at a point when the number of cells exceeded $8 \times 10^7$ cells/mL (Table 1). The culture solution was extracted so as to be at $7.3 \times 10^7$ cells/mL (cell bleeding) at a time when the number of cells exceeded $8 \times 10^7$ cells, and culture was performed while adjusting so as not to increase the cell density by supplementing the portion of the initial medium extracted. In order to measure the cell density, the culture solution components, and the antibody concentration over time, sampling of the culture solution in the culture tank and the culture solution on the permeation side were performed every day.

Figure 18:
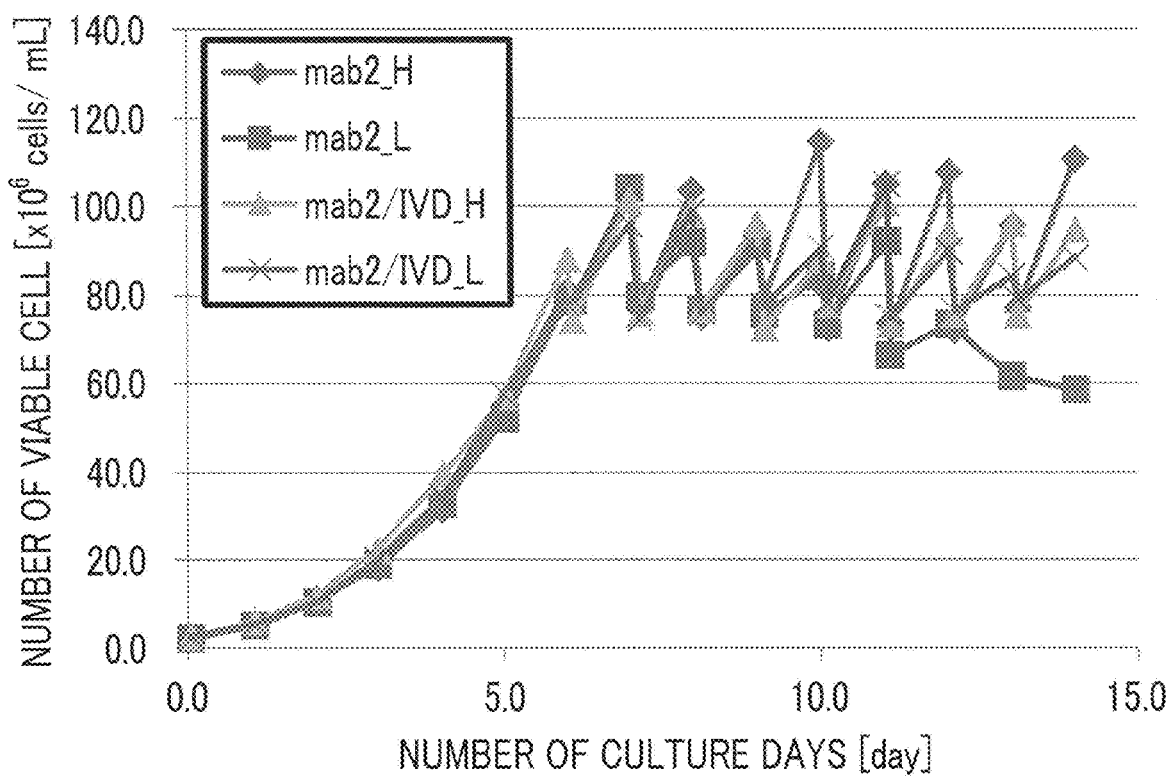
FIG. 18 illustrates a result of measuring the viable cell density of cells over time.
Figure 19:
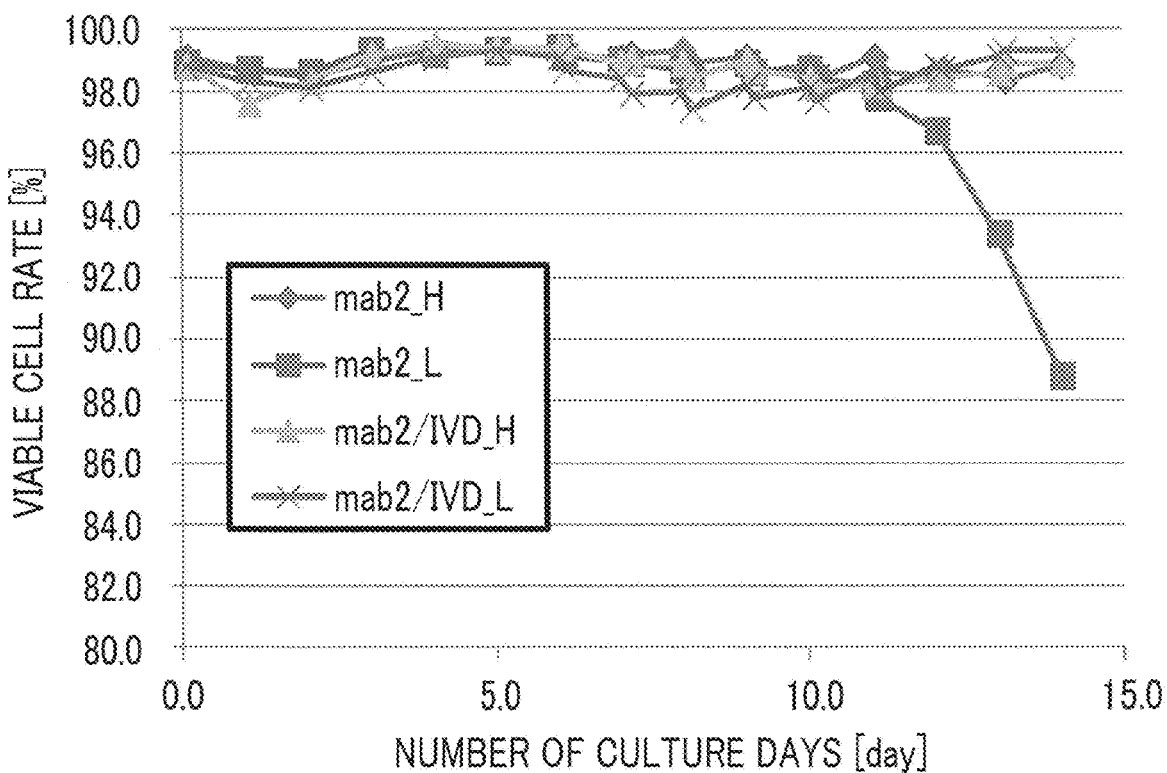
FIG. 19 illustrates a result of measuring the viable cell rate (survival rate) of cells over time.
Figure 20:
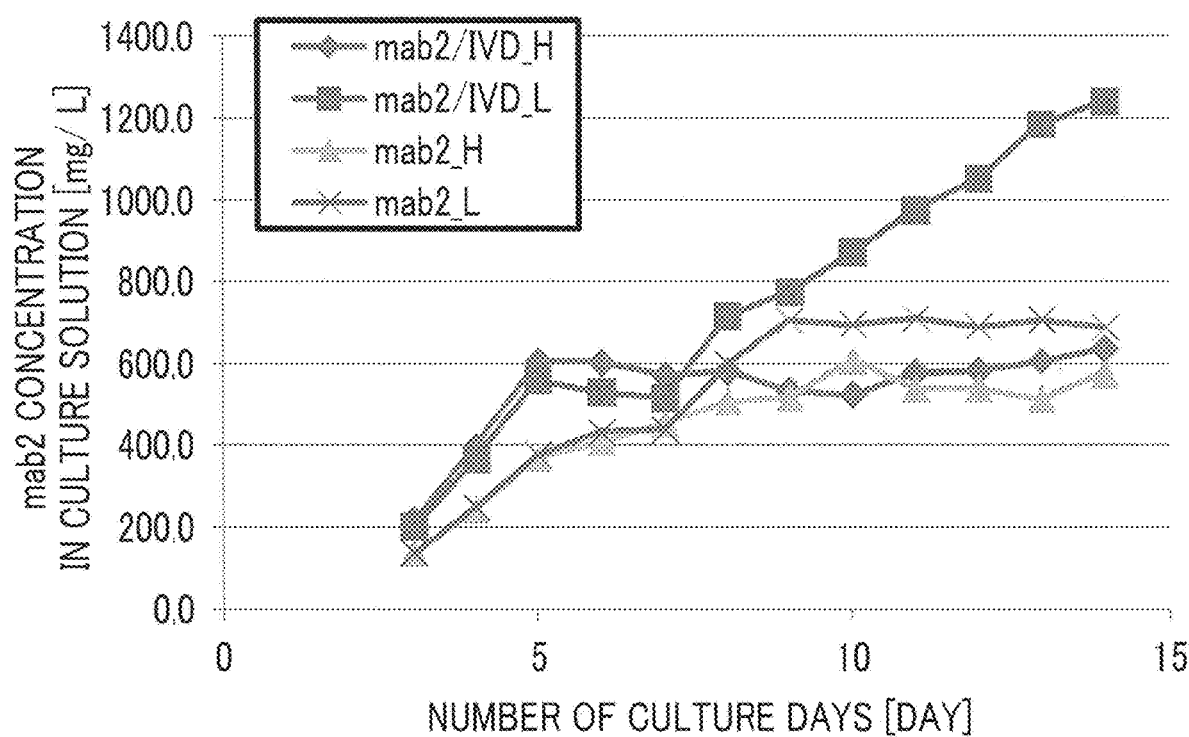
FIG. 20 illustrates a result of measuring the concentration of the monoclonal antibodies in a culture solution on a permeation side over time.
Figure 21:
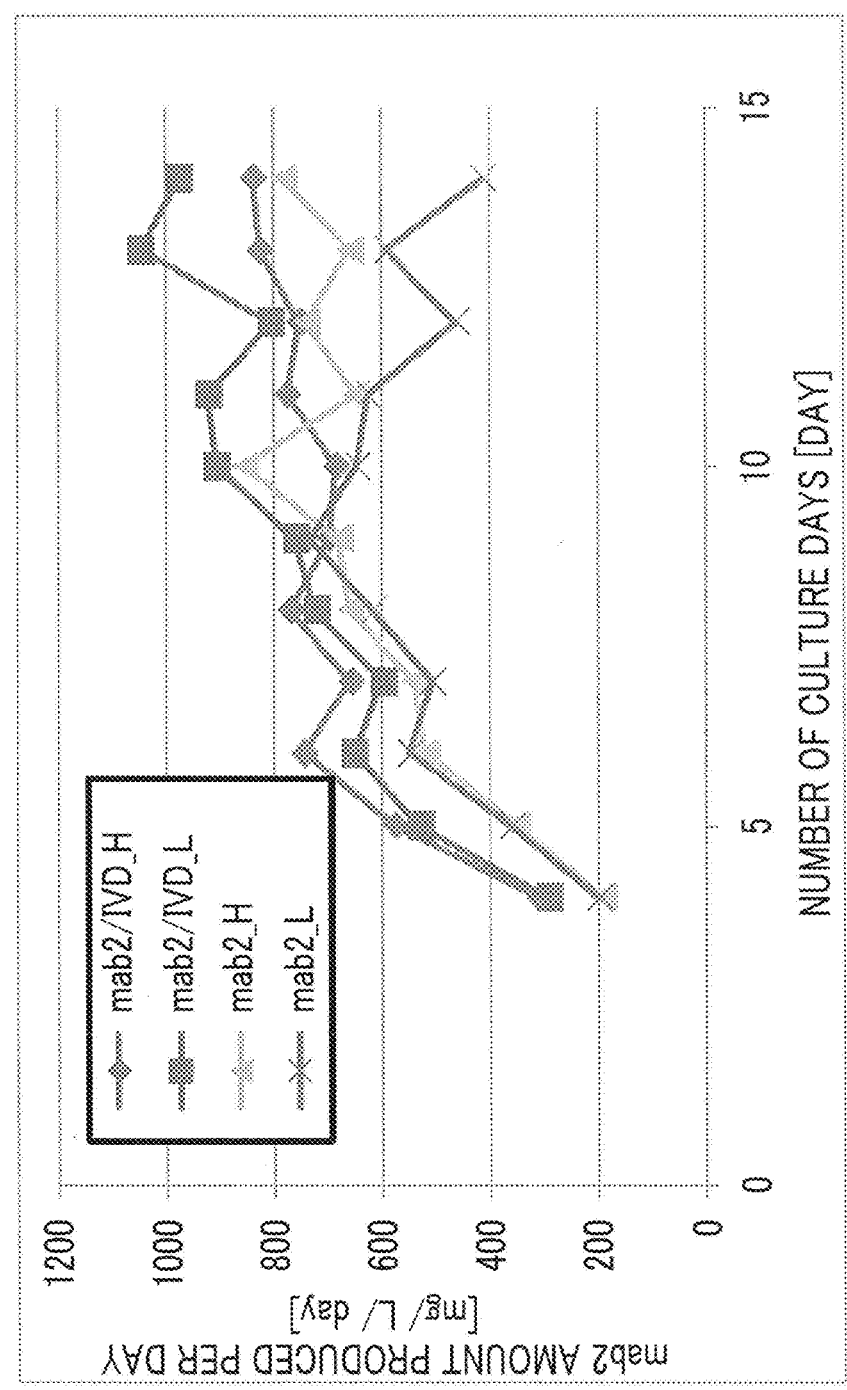
FIG. 21 illustrates a result of measuring a production amount of monoclonal antibodies per day.
Figure 22:
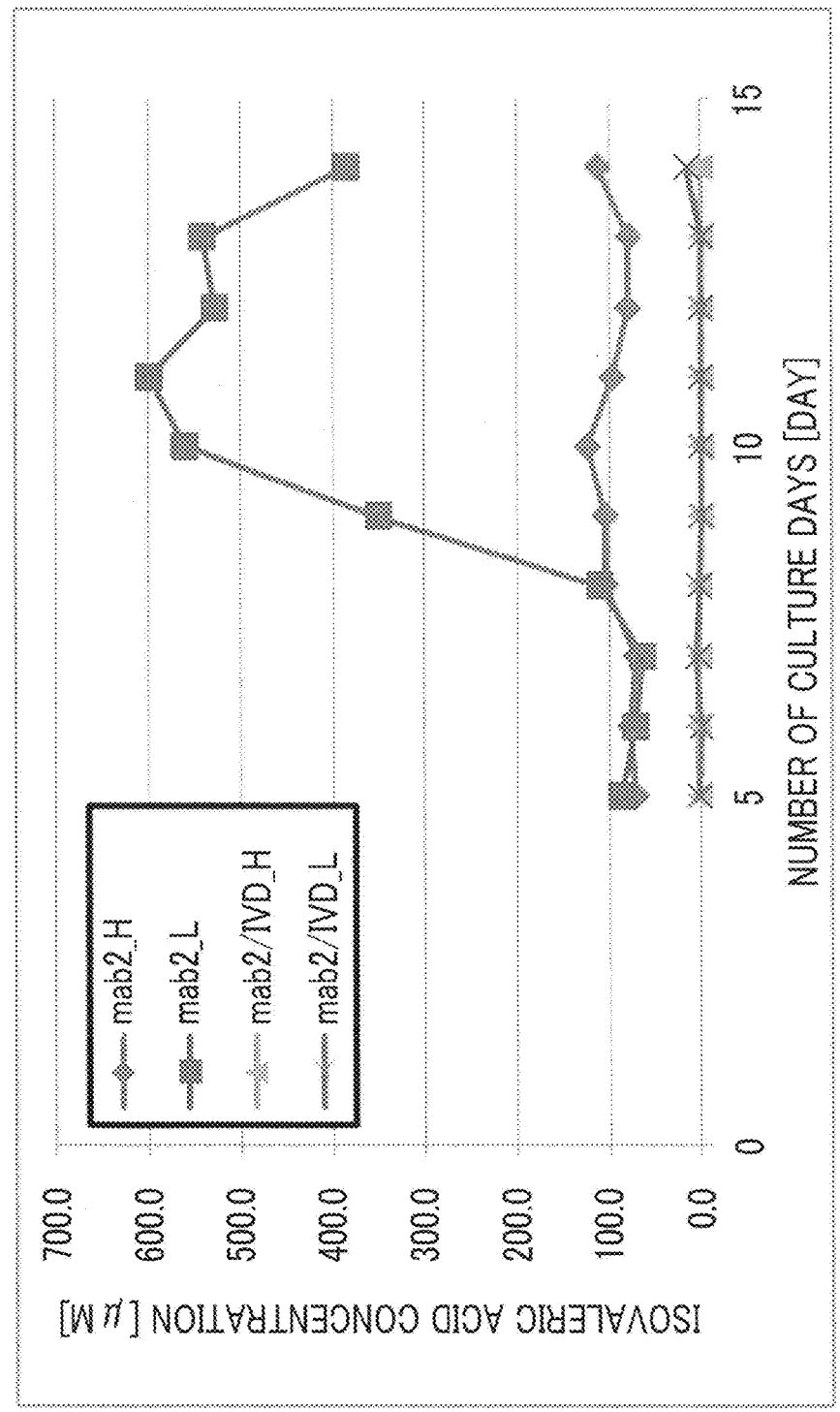
FIG. 22 illustrates a result of measuring a concentration of the isovaleric acid in a culture solution over time.
Figure 23:
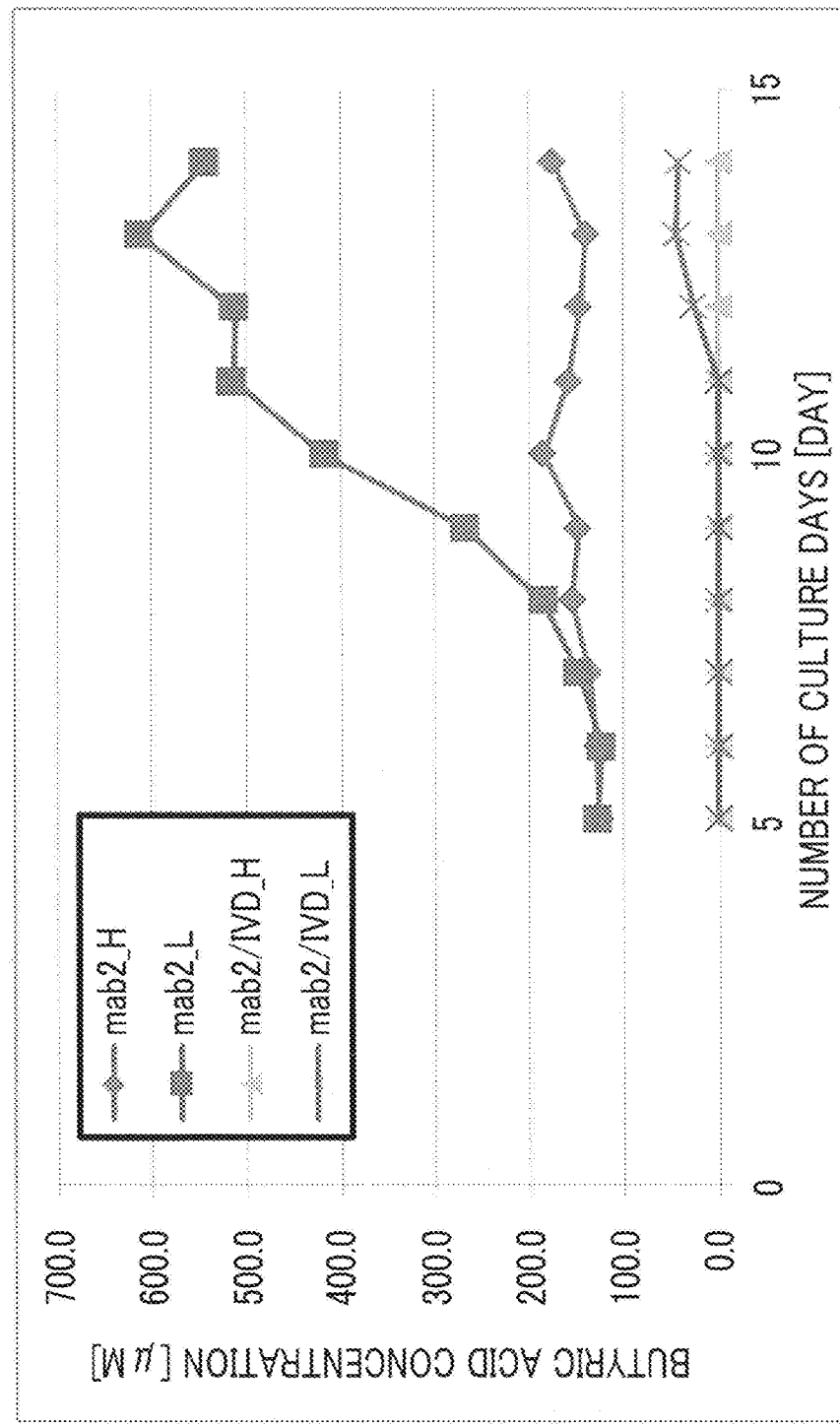
FIG. 23 illustrates a result of measuring a concentration of a butyric acid in a culture solution over time.

While mab2/IVD (CHO-DG44) cells were able to maintain the number of viable cells and the high viable cell rate in the perfusion culture even in a case where the perfusion ratio was reduced, it was observed that the number of cells and the viable cell rate were gradually decreased in the mab2 (CHO-DG44) cells (FIGS. 18 and 19). In the perfusion culture, the amount of mab2 produced by cells per day was calculated, and it was found that the mab2 productivity was decreased even in a case where the perfusion ratio of the mab2/IVD cells was decreased (FIGS. 20 and 21). In the mab2 cells, the isovaleric acid and the butyric acid in the culture supernatant from around day 6 when the perfusion ratio was reduced were accumulated, whereas in the mab2/IVD cells, accumulation of the isovaleric acid and the butyric acid in the supernatant solution was not found throughout 14 days of the culture period (FIGS. 22 and 23). The mab2/IVD cells were able to maintain proliferative properties at a low perfusion ratio by not accumulating a proliferation inhibitor in the culture tank, and enabled a high-density culture. In addition, in a case where the medium use amount in a case where culturing the mab2/IVD cells at a low perfusion ratio on a 2,000 L scale was estimated, it was found that it is possible to save 28,800 L of medium during the culture of 24 days (Table 2).

TABLE 1

Perfusion culture condition table

| | | Perfusion ratio (vvd) | | | | | |
|---|---|---|---|---|---|---|---|
| Level name | Vector | Day 0-2 | Day 3 | Day 4 | Day 5-6 | Day 7-10 | Day 11-14 |
| Mab2_H | pmab2 | 0.3 | 0.45 | 0.7 | 1.2 | 1.2 | 1.2 |
| Mab2_L | pmab2 | 0.3 | 0.45 | 0.7 | 1.2 | 0.8 | 0.6 |
| Mab2/IVD_H | pmab2/IVD | 0.3 | 0.45 | 0.7 | 1.2 | 1.2 | 1.2 |
| Mab2/IVD_L | pmab2/IVD | 0.3 | 0.45 | 0.7 | 1.2 | 0.8 | 0.6 |

The total amount of mab2 produced by cells per day $Y_{mab2}$ was obtained by the following formula.

$$Y_{mab2}=(Y_{Bt2}-Y_{Bt1})+P_{t1}\int_{t1}^{t2}Y_t dt \qquad \text{[Expression 3]}$$

$Y_{Tti}$ [g/L]=antibody concentration on permeation side on culture day ti $Y_{Tti'}$ [g/L]=antibody concentration on permeation side after bleeding on culture day ti $Y_{Bti}$ [g/L]=antibody concentration on culture tank side on culture day ti $P_{ti}$ [vvd]=perfusion ratio from culture day ti to t(i+1)

TABLE 2

Estimated culture use amount at time of performing culture in 2,000-L culture tank

| Level | Normal state perfusion ratio [vvd] | Normal state medium use amount[*1] [L/day] | Possibility of culture | Culture use amount at time of performing culture in normal state for 24 days |
|---|---|---|---|---|
| Mab2_H | 1.2 | 2400 | Possible | 57600 |
| Mab2_L | 0.6 | 1200 | Not possible | — |

TABLE 2-continued

Estimated culture use amount at time of performing culture in 2,000-L culture tank

| Level | Normal state perfusion ratio [vvd] | Normal state medium use amount[*1] [L/day] | Possibility of culture | Culture use amount at time of performing culture in normal state for 24 days |
|---|---|---|---|---|
| Mab2/IVD_H | 1.2 | 2400 | Possible | 57600 |
| Mab2/IVD_L | 0.6 | 1200 | Possible | 28800 |

[*1]The amount of medium supplemented during cell bleeding is excluded
[*2]The normal state is assumed to continue for 24 days

[Sequence List]
PCT_animal cells, animal cells_20181211_102636_5.txt

What is claimed is:

1. An animal cell that has an exogenous gene encoding a target protein and a foreign gene encoding an isovaleryl-CoA dehydrogenase,
   wherein the animal cell is a CHO cell,
   wherein the gene encoding the target protein and the foreign gene encoding isovaleryl-CoA dehydrogenase are present on the same expression vector, and
   wherein the gene encoding the target protein and the gene encoding isovaleryl-CoA dehydrogenous are operatively linked to different promoters.

2. The animal cell according to claim 1, wherein an expression level of the isovaleryl-CoA dehydrogenase is three times or more that of an animal cell not having a foreign gene encoding an isovaleryl-CoA dehydrogenase.

3. A method for producing the animal cell according to claim 1, the method comprising:
   introducing an expression vector comprising a gene encoding a target protein and a foreign gene encoding isovaleryl-CoA dehydrogenase into an animal cell,
   wherein the gene encoding the target protein and the gene encoding isovaleryl-CoA dehydrogenous are operatively linked to different promoters.

4. The method according to claim 3, wherein the step of introducing said expression vector is performed by electroporation.

5. A method for producing a target protein, comprising: culturing the animal cell according to claim 1.

6. The method according to claim 5, wherein the culture of the animal cell is a fed-batch culture or a batch culture.

7. The method according to claim 6, wherein the seeded cell density of a cell culture is $0.2 \times 10^6$ cells/mL to $5 \times 10^6$ cells/mL.

8. The method according to claim 6, wherein the viable cell rate during a culture period is 60% or more over the entire period.

9. The method according to claim 6, wherein the concentration of an isovaleric acid in a culture solution throughout the culture period is 3,000 pmol/L or less.

10. The method according to claim 6, wherein the secretion amount of the isovaleric acid per cell throughout the culture period is 30 fmol/cell/day or less.

11. The method according to claim 6, wherein the concentration of a butyric acid in the culture solution throughout the culture period is 3,000 kmol/L or less.

12. The method according to claim 5, wherein the culture of the animal cell is a perfusion culture.

13. The method according to claim 12, wherein the seeded cell density of the cell culture is $0.2 \times 10^6$ cells/mL to $3 \times 10^7$ cells/mL.

14. The method according to claim 12, wherein the viable cell rate during the culture period is 90% or more over the entire period.

15. The method according to claim 12, wherein the concentration of the isovaleric acid in the culture solution is 3,000 kmol/L or less.

16. The method according to claim 12, wherein the secretion amount of the isovaleric acid per cell is 30 fmol/cell/day or less.

17. The method according to claim 12, wherein the concentration of the butyric acid in the culture solution throughout the culture period is 3,000 pmol/L or less.

18. The method according to claim 12, wherein a secretion amount of the butyric acid per cell throughout the culture period is 30 fmol/cell/day or less.

* * * * *